(12) United States Patent
Ogasawara et al.

(10) Patent No.: US 8,945,012 B2
(45) Date of Patent: Feb. 3, 2015

(54) ULTRASONIC DIAGNOSTIC APPARATUS AND COMPUTER PROGRAM PRODUCT

(75) Inventors: Yoichi Ogasawara, Nasushiobara (JP); Yoshihiro Oomori, Otawara (JP); Kazuya Akaki, Nasushiobara (JP); Osamu Nakajima, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 648 days.

(21) Appl. No.: 12/558,724

(22) Filed: Sep. 14, 2009

(65) Prior Publication Data
US 2010/0069756 A1    Mar. 18, 2010

(30) Foreign Application Priority Data

Sep. 17, 2008 (JP) ................. 2008-237661

(51) Int. Cl.
| | |
|---|---|
| *A61B 8/00* | (2006.01) |
| *A61B 8/08* | (2006.01) |
| *G01S 7/52* | (2006.01) |
| *G01S 15/89* | (2006.01) |
| *A61B 5/00* | (2006.01) |
| *A61B 8/13* | (2006.01) |

(52) U.S. Cl.
CPC . *A61B 8/08* (2013.01); *A61B 8/483* (2013.01); *A61B 8/54* (2013.01); *G01S 7/52039* (2013.01); *G01S 7/52085* (2013.01); *G01S 15/8993* (2013.01); *A61B 5/4244* (2013.01); *A61B 8/13* (2013.01); *G01S 7/52063* (2013.01)
USPC .......................................... 600/443; 600/437

(58) Field of Classification Search
USPC ................................... 600/437, 443, 444, 447
See application file for complete search history.

(56) References Cited

U.S. PATENT DOCUMENTS 5,879,303 A * 3/1999 Averkiou et al. ............. 600/447
6,039,690 A * 3/2000 Holley et al. ................. 600/440
(Continued)

FOREIGN PATENT DOCUMENTS

| JP | 7-328007 A | 12/1995 |
|---|---|---|
| JP | 8-126641 A | 5/1996 |

(Continued)

OTHER PUBLICATIONS

U.S. Appl. No. 12/794,055, filed Jun. 4, 2010, Ogasawara, et al.
(Continued)

*Primary Examiner* — Unsu Jung
*Assistant Examiner* — Phong K Huynh
(74) *Attorney, Agent, or Firm* — Oblon, Spivak, McClelland, Maier & Neustadt, L.L.P.

(57) ABSTRACT

A region-of-interest setting unit sets a region of interest to be included in an ultrasound image. A first movement-amount calculating unit sequentially calculates a movement amount of the set region of interest between reception data along the time sequence as a first movement amount. A transmitting-receiving delay-amount computing unit computes a delay amount for sequentially shifting a scan region of an ultrasonic beam based on the sequentially calculated first movement amount. A computation/control circuit performs control so as to generate a high voltage pulse based on the computed delay amount. A second movement-amount calculating unit sequentially calculates a movement amount of the region of interest between image data along the time sequence as a second movement amount. A display-position correcting unit performs a correction such that the region of interest included in the image data is to be displayed at the same display position, based on the second movement amount.

20 Claims, 10 Drawing Sheets

(56) References Cited

U.S. PATENT DOCUMENTS

| | | | |
|---|---|---|---|
| 6,322,505 B1* | 11/2001 | Hossack et al. | 600/443 |
| 6,589,176 B2 | 7/2003 | Jago et al. | |
| 2005/0096538 A1* | 5/2005 | Chomas et al. | 600/437 |
| 2008/0200808 A1* | 8/2008 | Leidel et al. | 600/443 |

FOREIGN PATENT DOCUMENTS

| | | |
|---|---|---|
| JP | 2000-132664 | 5/2000 |
| JP | 2005-511129 A | 4/2005 |
| JP | 2006-271523 A | 10/2006 |
| JP | 2006-280768 A | 10/2006 |
| JP | 2007-29335 | 2/2007 |
| JP | 2007-75333 A | 3/2007 |
| JP | 2008-12141 A | 1/2008 |
| JP | 2008-206748 A | 9/2008 |

OTHER PUBLICATIONS

Japanese Office Action Issued Mar. 5, 2013 in Patent Application No. 2008-237661 (with English translation).

* cited by examiner

ULTRASONIC DIAGNOSTIC APPARATUS AND COMPUTER PROGRAM PRODUCT

CROSS-REFERENCE TO RELATED APPLICATIONS

This application is based upon and claims the benefit of priority from the prior Japanese Patent Application No. 2008-237661, filed on Sep. 17, 2008; the entire contents of which are incorporated herein by reference.

BACKGROUND OF THE INVENTION

1. Field of the Invention

The present invention relates to an ultrasonic diagnostic apparatus and a computer program product.

2. Description of the Related Art

Conventionally, an ultrasonic diagnostic apparatus has advantages, such as simple and easy operability and noninvasiveness without risk of radiation exposure, compared with other medical image diagnostic apparatuses, for example, an X-ray diagnostic apparatus and an X-ray Computed Tomography (CT) apparatus; and is used in a medical practice of today for an examination or a diagnosis of the condition of a tissue among various living body tissues, for example, a heart, a liver, a kidney, a mammary gland, or a muscle.

An ultrasonic diagnostic apparatus transmits an ultrasonic wave from an ultrasonic probe in contact with a body surface of a subject, and receives an ultrasonic wave reflected from an internal tissue of the subject, thereby creating an ultrasound image. A general ultrasonic diagnostic apparatus creates a tomogram (two-dimensional image) of a tissue inside the subject by scanning a certain cross section with an ultrasonic wave, by using a one-dimensional ultrasonic probe in which a plurality of ultrasonic transducers is arranged in one row in the scanning direction.

Moreover, recently, an ultrasonic diagnostic apparatus has come into practical use, which creates a three-dimensional ultrasound image (volume data) substantially in real time by using a mechanical scan probe that performs a two-dimensional scan with an ultrasonic wave by mechanically sliding a one-dimensional ultrasonic probe, or by using a two-dimensional ultrasonic probe that performs a two-dimensional scan with ultrasonic waves from a plurality of ultrasonic transducers arranged in a matrix (for example, see JP-A 2000-13266 (KOKAI)).

For a diagnosis by using an ultrasonic diagnostic apparatus, a realtime responsiveness of an ultrasound image created by the ultrasonic diagnostic apparatus is required as well as improvement in the image quality of the ultrasound image created by the ultrasonic diagnostic apparatus.

Parameters for improving the image quality of an ultrasound image includes focus processing by delay control of a transmitting-receiving system, filtering processing by echo filter, sensitivity improvement processing by improving reception dynamic range, signal processing on reception data, and processing for improving a spatial resolution in an lateral direction, which is particularly required among them.

To improve a spatial resolution in the lateral direction, an increase in the scanning density of ultrasonic waves transmitted from the ultrasonic probe is basically required. When the scanning density is increased, the number of scan lines per unit area or unit volume is increased. Even when creating an ultrasound image focused on the same depth, a required scan time with an ultrasonic wave is increased proportionally to the number of scan lines. Therefore, if scanning density is increased to improve the image quality of an ultrasound image, a scan rate that is the number of scan lines per unit time is decreased, so that realtime responsiveness is lost.

Moreover, a technology of ensuring realtime responsiveness has been known by widening the cover area of each ultrasonic wave to be transmitted from an ultrasonic probe, and reducing a scan time through parallel simultaneous reception of acquiring reception data of different scan lines in one-time of a transmission. In such case, the image quality of a created ultrasound image is lower than that in a case of acquiring reception data of one scan line in one-time of a transmission. Therefore, to achieve both of image-quality improvement and realtime responsiveness of an ultrasound image in a diagnosis by using an ultrasonic diagnostic apparatus, it is required to narrow a scan region of an ultrasonic wave as much as possible.

For this reason, a conventional ultrasonic diagnostic apparatus includes a function of determining a scan region of an ultrasonic wave in advance by referring to an ultrasound image so as to include a region of interest of a diagnosis subject in the ultrasound image. In this way, a scan for an ultrasound image is performed after a scan region is determined, and then an ultrasound image corresponding to the fixed scan region is displayed on a monitor included in the ultrasonic diagnostic apparatus.

According to the conventional technology described above, when the region of interest moves, there is a problem that a stress on a subject and a burden on an operator tend to be large in order to achieve both image-quality improvement and realtime responsiveness of an ultrasound image.

In other words, when an organ itself that is the diagnosis subject cyclically moves due to a breath, a region of interest inside the organ also cyclically moves simultaneously. Because of such motion, to include a region of interest that cyclically moves due a breath surely in an ultrasound image, a scan region of an ultrasonic wave needs to be widened.

When performing a diagnosis on a liver in an abdomen region, because the liver itself to be a diagnosis subject is large, a scan region of an ultrasonic wave is required to be wide, and furthermore, the image quality of an ultrasound image is required to be improved because change in tissue characterization of a tissue inside the liver is influential information as a diagnostic reference. A liver itself cyclically moves due to a breath, so that a scan region of an ultrasonic wave is required to be further widened to ensure that an ultrasound image includes, for example, a tumor inside the liver as a region of interest.

In this way, when a region of interest moves, a scan region is widened to ensure that the region of interest is to be included in an ultrasound image as well as to improve the image quality, the number of scan lines tends to increase, as a result, realtime responsiveness tends to be lost.

To secure realtime responsiveness, a doctor or an engineer who is an operator of the ultrasonic diagnostic apparatus needs to narrow a scan region of an ultrasonic wave as much as possible as described above. For this reason, the operator needs to ask a subject to hold the subject's breath while acquiring an ultrasound image such that an organ itself does not cyclically move due to a breath.

However, "to hold the breath" is not generally easy for a subject, and it is a difficult action particularly for a subject who has a respiratory disease or a subject of a relatively high age. When another scan is repeated because an ultrasound image did not include a region of interest, a subject is required "to hold the breath" more times.

Consequently, in order to avoid stress on the subject, the operator has to continue manually operating the ultrasonic probe in accordance with the breath of the subject for the region of interest to be included in the ultrasound image; however, when creating a tomogram by using a one-dimensional ultrasonic probe, it is not an easy operation to continue adjusting the position of the one-dimensional ultrasonic probe for a moving region of interest to be included in the tomogram, thereby increasing a burden on the operator.

On the other hand, when creating a three-dimensional ultrasound image by using a mechanical scan probe or a two-dimensional ultrasonic probe, a scan region is to be wider than that when creating a tomogram. For this reason, to ensure the image quality (the spatial resolution in an lateral direction) of an ultrasound image and the realtime responsiveness both of which are equivalent to those when creating a tomogram, a scan region of an ultrasonic wave needs to be narrowed.

When creating a three-dimensional ultrasound image, a necessity for the subject "to hold the breath" not to move the region of interest turns more serious than when creating a tomogram; consequently, to avoid stress on the subject, the operator needs to continue manually operating a mechanical scan probe or a two-dimensional ultrasonic probe in accordance with the breath of the subject, similarly to when creating a tomogram.

In such case, ultrasonic waves are two-dimensionally transmitted, so that it is possibly easier to adjust the position of the ultrasonic probe for the region of interest to be constantly included in an ultrasound image than a case of creating a tomogram (two-dimensional image); however, it does not reduce a burden on the operator. Moreover, even though the position of the ultrasonic probe is adjusted, it cannot be ensured that a moving region of interest is to be constantly included in a three-dimensional ultrasound image, consequently, the subject sometimes needs "to hold the breath" in some cases in order to avoid repeating a scan.

Furthermore, generally, a created three-dimensional ultrasound image is scarcely used as it is, and the operator cuts out a cross section that includes the region of interest from a three-dimensional ultrasound image, and then performs a diagnosis by referring to the cut out cross section; therefore, when performing a diagnosis by creating a three-dimensional ultrasound image, a burden on the operator becomes large.

SUMMARY OF THE INVENTION

According to one aspect of the present invention, an ultrasonic diagnostic apparatus includes a region-of-interest setting unit that sets a region of interest to be included in an ultrasound image created based on reception data acquired by using an ultrasonic wave reflected from a subject; an inter-reception-data movement-amount calculating unit that calculates a movement amount of the region of interest set by the region-of-interest setting unit between reception data along a time sequence acquired by using an ultrasonic wave reflected from the subject, as an inter-reception-data movement amount; a scan-region control unit that controls a scan region of an ultrasonic wave to be transmitted from an ultrasonic probe such that the scan region is to be shifted based on the inter-reception-data movement amount calculated by the inter-reception-data movement-amount calculating unit; an image creating unit that creates a plurality of ultrasound images along a time sequence based on reception data corresponding to an ultrasonic wave transmitted from the ultrasonic probe into the scan region shifted according to control by the scan-region control unit; and a display control unit that controls a display such that the ultrasound images along the time sequence created by the image creating unit are displayed on a predetermined display unit.

According to another aspect of the present invention, a computer program product having a computer readable medium including programmed instructions for executing computer executable image processing, wherein the instructions, when executed by a computer, cause the computer to perform: setting a region of interest to be included in an ultrasound image created based on reception data acquired by using an ultrasonic wave reflected from a subject; calculating a movement amount of set region of interest between reception data along a time sequence acquired by using an ultrasonic wave reflected from the subject, as an inter-reception-data movement amount; controlling a scan region of an ultrasonic wave to be transmitted from an ultrasonic probe such that the scan region is to be shifted based on calculated inter-reception-data movement amount; creating a plurality of ultrasound images along a time sequence based on reception data corresponding to an ultrasonic wave transmitted from the ultrasonic probe into shifted scan region; and controlling a display such that created ultrasound images along the time sequence are displayed on a predetermined display unit.

DETAILED DESCRIPTION OF THE INVENTION

Exemplary embodiments of an ultrasonic diagnostic apparatus and a computer program product according to the present invention will be explained below in detail with reference to the accompanying drawings.

Figure 1:
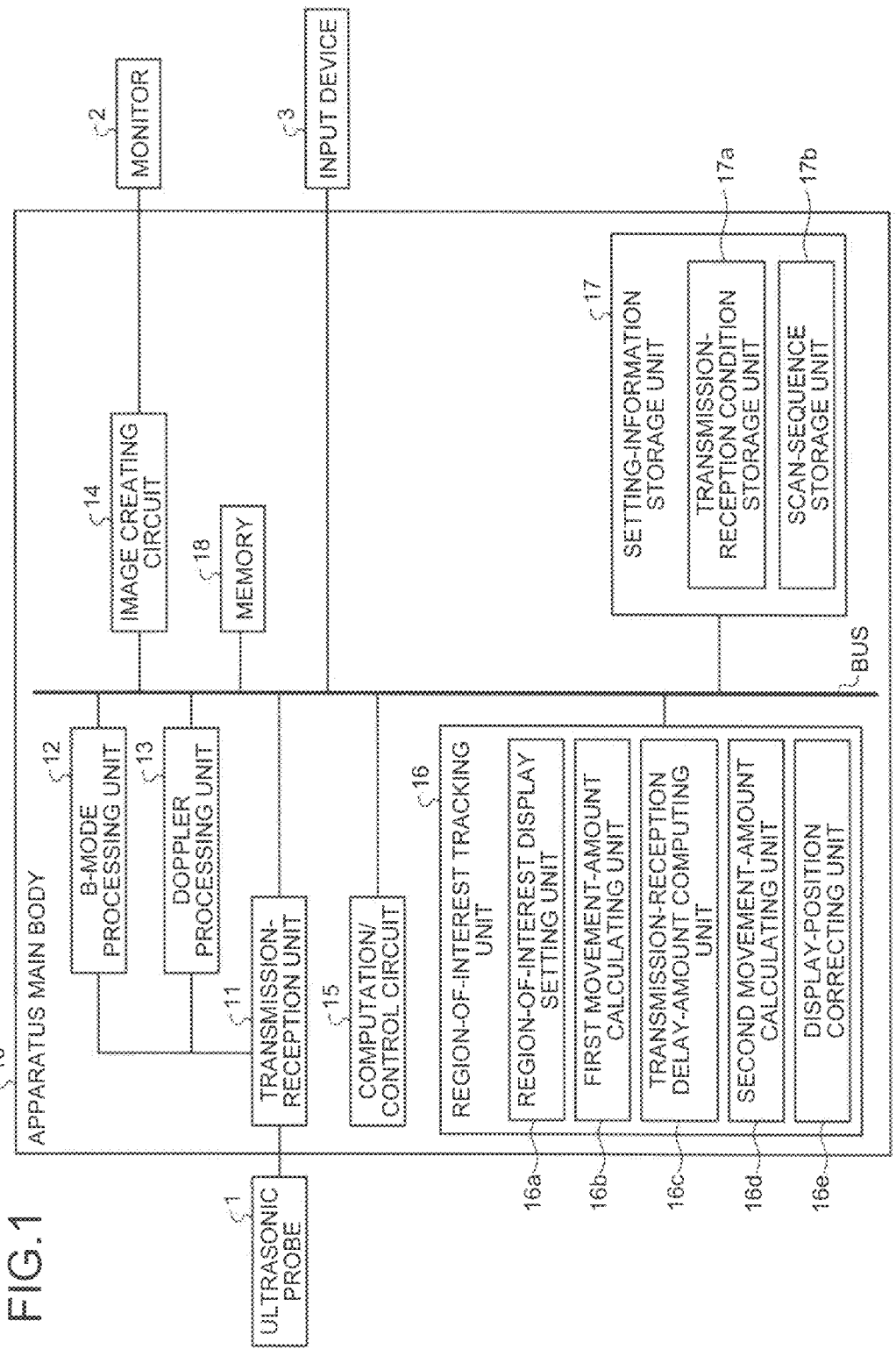
FIG. 1 is a schematic diagram for explaining of a configuration of an ultrasonic diagnostic apparatus according to a first embodiment of the present invention.

First of all, a configuration of an ultrasonic diagnostic apparatus according to a first embodiment of the present invention is explained below. FIG. 1 is a schematic diagram for explaining of a configuration of an ultrasonic diagnostic apparatus according to a first embodiment. As shown in FIG. 1, the ultrasonic diagnostic apparatus according to the first embodiment includes an ultrasonic probe 1, a monitor 2, an input device 3, and an apparatus main body 10.

The ultrasonic probe 1 includes a plurality of built-in ultrasonic transducers (not-shown) that is a plurality of transducer cells is integrated, transmits an ultrasonic wave generated from the ultrasonic transducer to the inside of the subject as an ultrasonic beam, and receives a reflected wave of the ultrasonic beam with each transducer cell of the ultrasonic transducers.

The first embodiment is explained below in a case of using a two-dimensional ultrasonic probe as the ultrasonic probe 1 that includes ultrasonic transducers arranged in a matrix, and transmits a two-dimensional ultrasonic beam to the inside of the subject. Moreover, according to the first embodiment, the ultrasonic probe 1 is also capable to scan the inside of the subject along a two-dimensional cross section by transmitting a one-dimensional ultrasonic beam as well as three-dimensionally scanning the inside of the subject by transmitting a two-dimensional ultrasonic beam.

The monitor 2 is a display device that displays an ultrasound image created by the apparatus main body 10. The input device 3 includes a panel switch, a touch command screen, a foot switch, a trackball, and the like, receives various setting requests from a doctor or an engineer as an operator of the ultrasonic diagnostic apparatus, and inputs each of the received setting requests into the apparatus main body 10.

The apparatus main body 10 is a device that creates an ultrasound image based on a reflected wave received by the ultrasonic probe 1; and includes a transmitting-receiving unit 11, a B-mode processing unit 12, a doppler processing unit 13, an image creating circuit 14, a computation/control circuit 15, a region-of-interest tracking unit 16, a setting-information storage unit 17, and a memory 18, as shown in FIG. 1.

The transmitting-receiving unit 11 is connected to the ultrasonic probe 1, a pulsar (not-shown) built in the transmitting-receiving unit 11 generates a high voltage pulse on each predetermined delay time in accordance with the control by the computation/control circuit 15. The high voltage pulse generated by the pulser built in the transmitting-receiving unit 11 is sequentially applied to each transducer cell of the ultrasonic transducer built in the ultrasonic probe 1, thereby generating an ultrasonic wave at each transducer cell.

Moreover, when a reception signal of the reflected wave received by the ultrasonic probe 1 is input, the transmitting-receiving unit 11 performs a gain correction on the reception signal with a preamplifier (not-shown), and an analog-to-digital (A/D) converting of the reception signal of which gain is corrected. The transmitting-receiving unit 11 then temporarily stores the A/D-converted reception signal into the memory 18 via a bus.

Furthermore, the transmitting-receiving unit 11 reads the A/D-converted reception signal stored in the memory 18 with required timing in accordance with the control by the computation/control circuit 15, and turns the read A/D-converted reception signal into reception data by phase rectifying addition. The transmitting-receiving unit 11 then transmits the reception data to the B-mode processing unit 12 and the doppler processing unit 13 via the bus in accordance with the control by the computation/control circuit 15.

The B-mode processing unit 12 performs data creation processing for B-mode image composition based on the received reception data, and the doppler processing unit 13 performs data creation processing for doppler-mode image composition based on the received reception data. The B-mode processing unit 12 or the doppler processing unit 13 then transmits data for B-mode image composition or the data for doppler-mode image composition to the image creating circuit 14, and also stores it into the memory 18.

The B-mode processing unit 12 and the doppler processing unit 13 can process both two-dimensional data and three-dimensional data, and perform data creation processing for image composition based on three-dimensional reception data created from a three-dimensional reception signal received by the ultrasonic probe 1 that is a two-dimensional ultrasonic probe, according to the first embodiment.

The image creating circuit 14 creates a B-mode image, a doppler image, or a superposed image of a B-mode image and a doppler image, by performing transformation process into a rectangular coordinate system (orthogonal transformation process) and digital-to-analog (D/A) conversion process on data for image composition received from the B-mode processing unit 12 or the doppler processing unit 13, and the created image is displayed on the monitor 2. The B-mode processing unit 12, the doppler processing unit 13, and the image creating circuit 14 correspond to "an image creating unit" described in the claims.

The setting-information storage unit 17 stores setting information for controlling the whole of the ultrasonic diagnostic apparatus. A transmission-reception condition storage unit 17a stores transmission and reception conditions for controlling transmission and reception of a high voltage pulse and transmission and reception of a reception signal between the transmitting-receiving unit 11 and the ultrasonic probe 1, transmission and reception of an A/D-converted reception signal between the transmitting-receiving unit 11 and the memory 18, transmission and reception of reception data between the transmitting-receiving unit 11 and the B-mode processing unit 12 or the doppler processing unit 13, transmission and reception of image data between the B-mode processing unit 12 or the doppler processing unit 13 and the memory 18, and the like.

The computation/control circuit 15 controls respective processes performed by the transmitting-receiving unit 11, the B-mode processing unit 12, the doppler processing unit 13, the image creating circuit 14, and the memory 18, based on each of the various setting requests input from the input device 3, and transmission and reception conditions stored by the transmission-reception condition storage unit 17a included in the setting-information storage unit 17.

The various setting requests input by the operator via the input device 3 include, for example, a request to set a cross-section for display for setting the cross-sectional direction of an ultrasound image as a two-dimensional image to be displayed on the monitor 2 from volume data created based on a three-dimensional reception signal received by the ultrasonic probe 1, and a request to set an image for display for setting the type of a two-dimensional image to be displayed on the monitor 2, such as a B-mode image, a doppler image, or a superposed image of a B-mode image and a doppler image.

In this way, the ultrasonic diagnostic apparatus according to the first embodiment transmits an ultrasonic beam to the subject from the ultrasonic probe 1, creates reception data by the transmitting-receiving unit 11 from a reception signal reflected from an internal tissue of the subject, creates volume data as data for image composition created by the B-mode processing unit 12 or the doppler processing unit 13 based on the reception data, creates a two-dimensional ultrasound image by the image creating circuit 14 from the volume data, and displays the created two-dimensional ultrasound image on the monitor 2.

As shown in FIG. 1, when the region of interest moves, the ultrasonic diagnostic apparatus according to the first embodiment can reduce a stress on the subject and a burden on the operator while maintaining the image quality and the realtime responsiveness of an ultrasound image, by using a region-of-interest display setting unit 16a, a first movement-amount calculating unit 16b, a transmission-reception delay-amount computing unit 16c, a second movement-amount calculating unit 16d, and a display-position correcting unit 16e, all of which are included in the region-of-interest tracking unit 16, and a scan-sequence storage unit 17b included in the setting-information storage unit 17.

Figure 2:
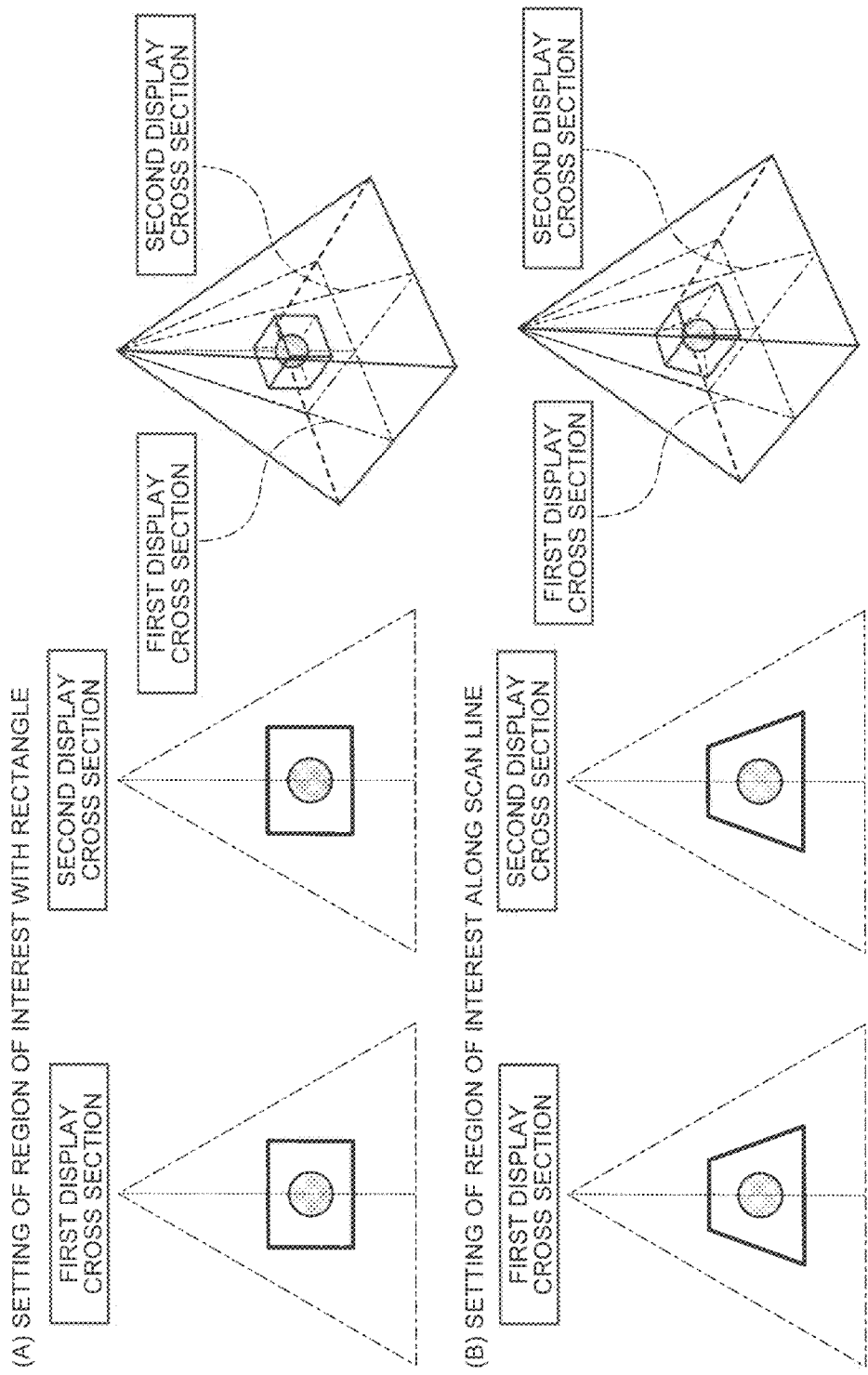
FIG. 2 is a schematic diagram for explaining a region-of-interest display setting unit.
Figure 3:
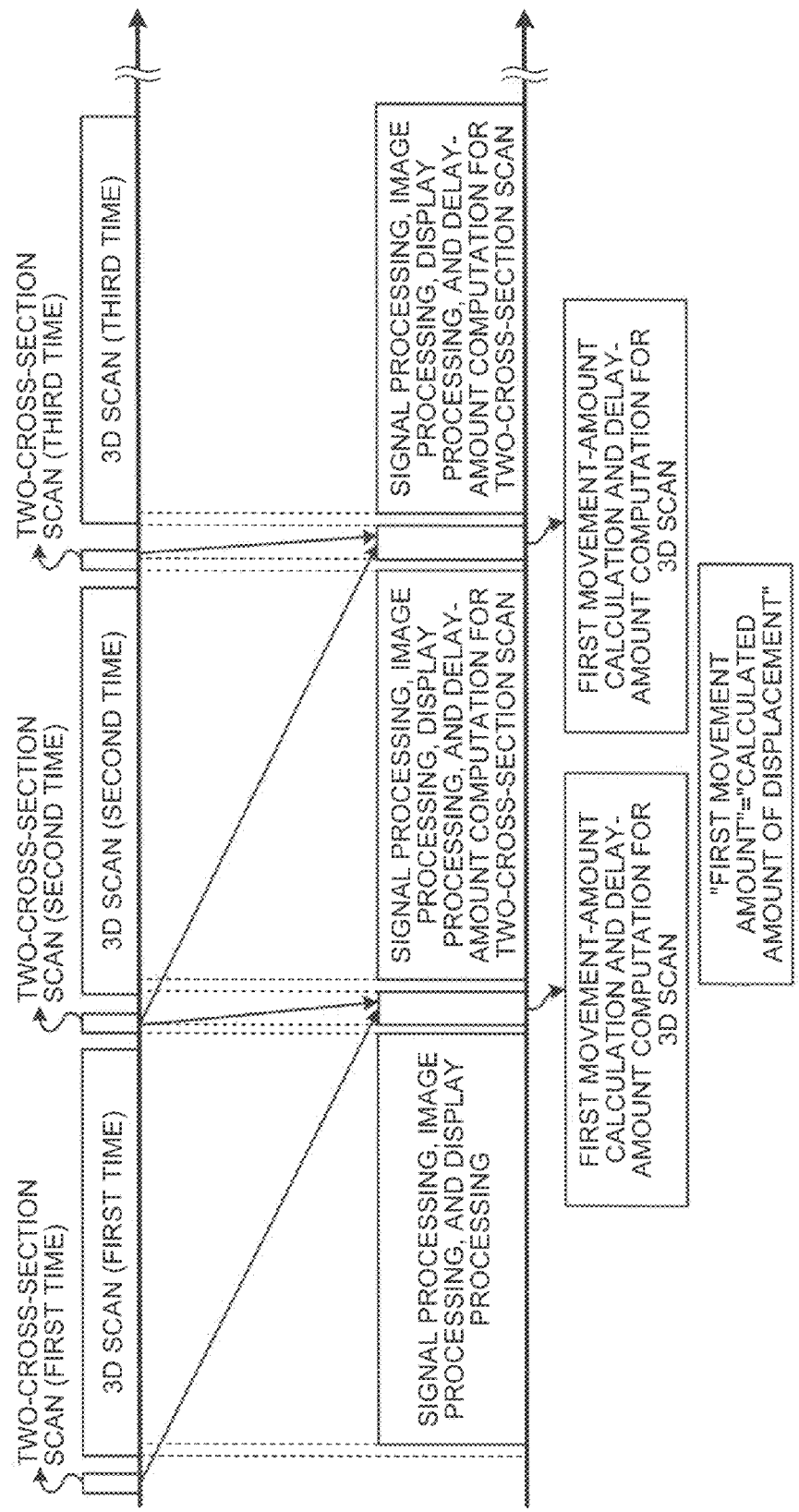
FIG. 3 is a schematic diagram for explaining a first scan sequence.
Figure 4:
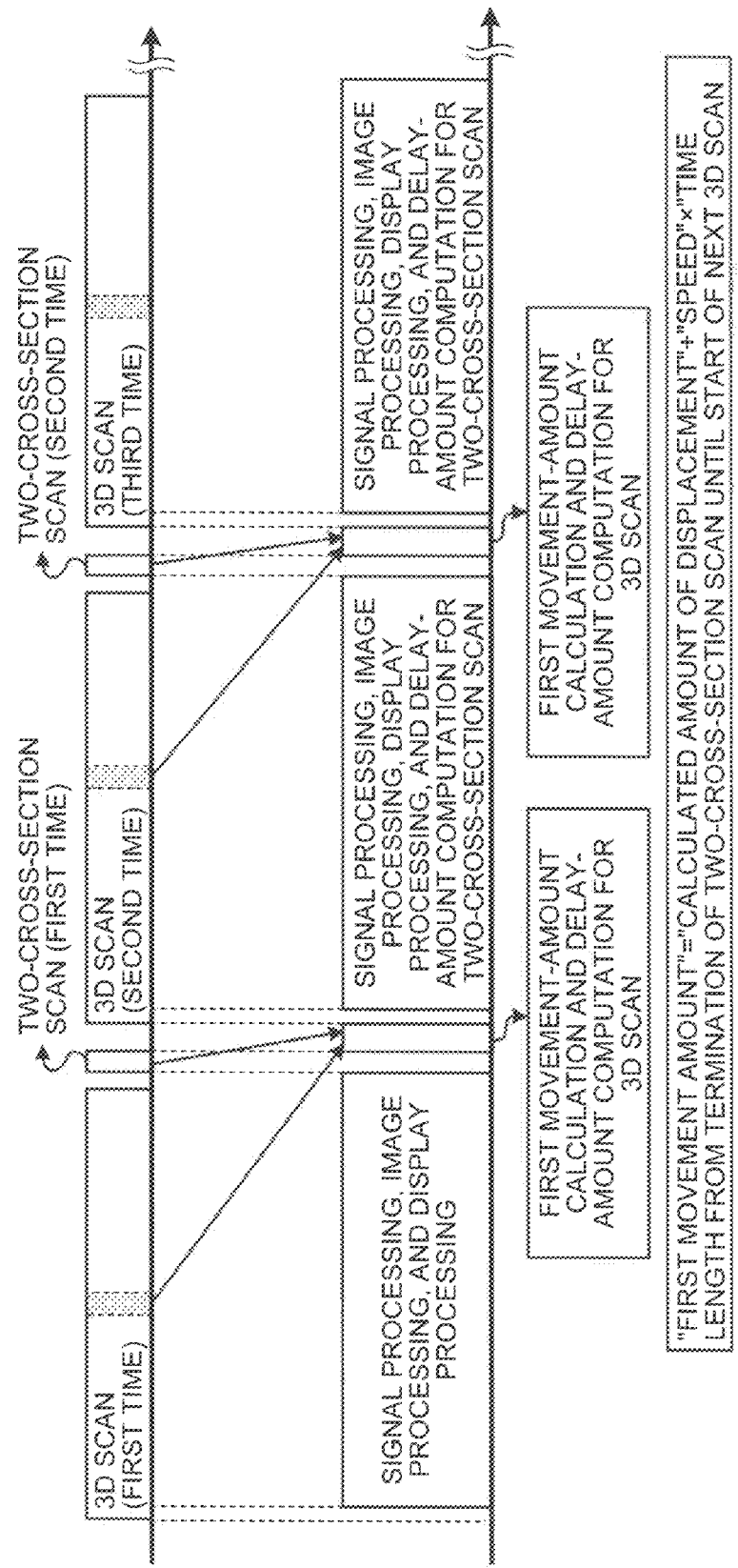
FIG. 4 is a schematic diagram for explaining a second scan sequence.
Figure 5:
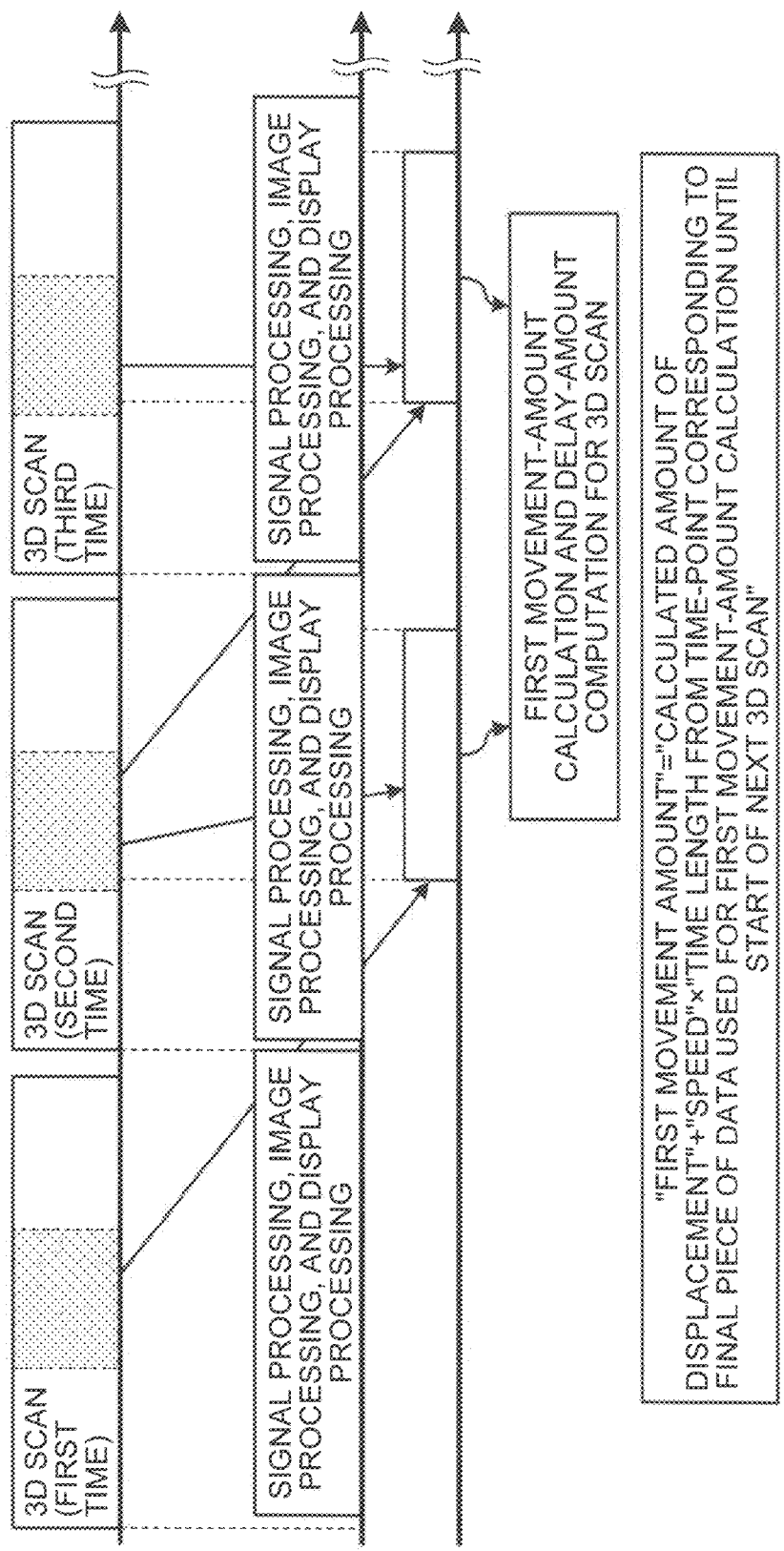
FIG. 5 is a schematic diagram for explaining a third scan sequence.
Figure 6:
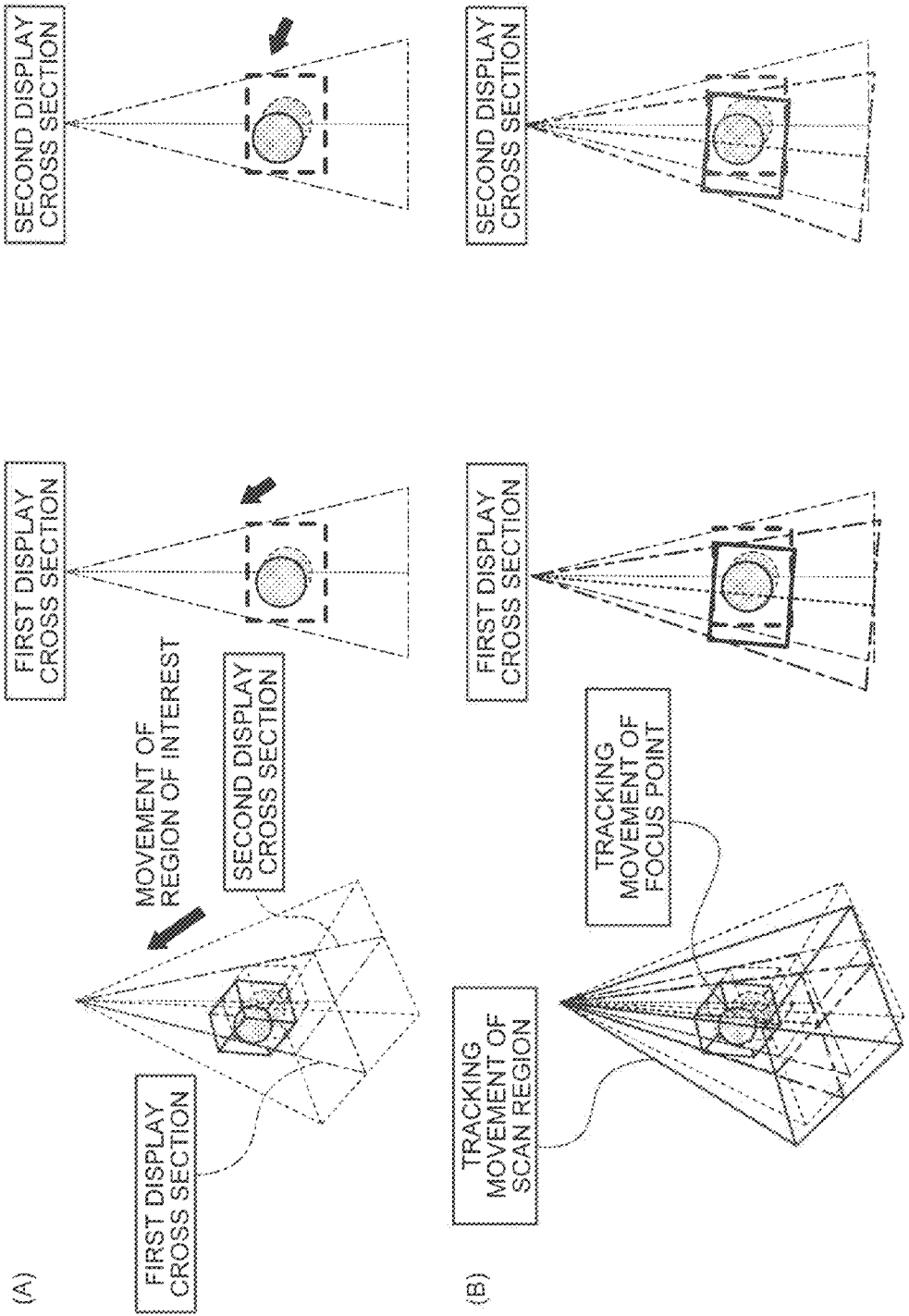
FIG. 6 is a schematic diagram for explaining a transmission-reception delay-amount computing unit and a computation/control circuit.
Figure 7:
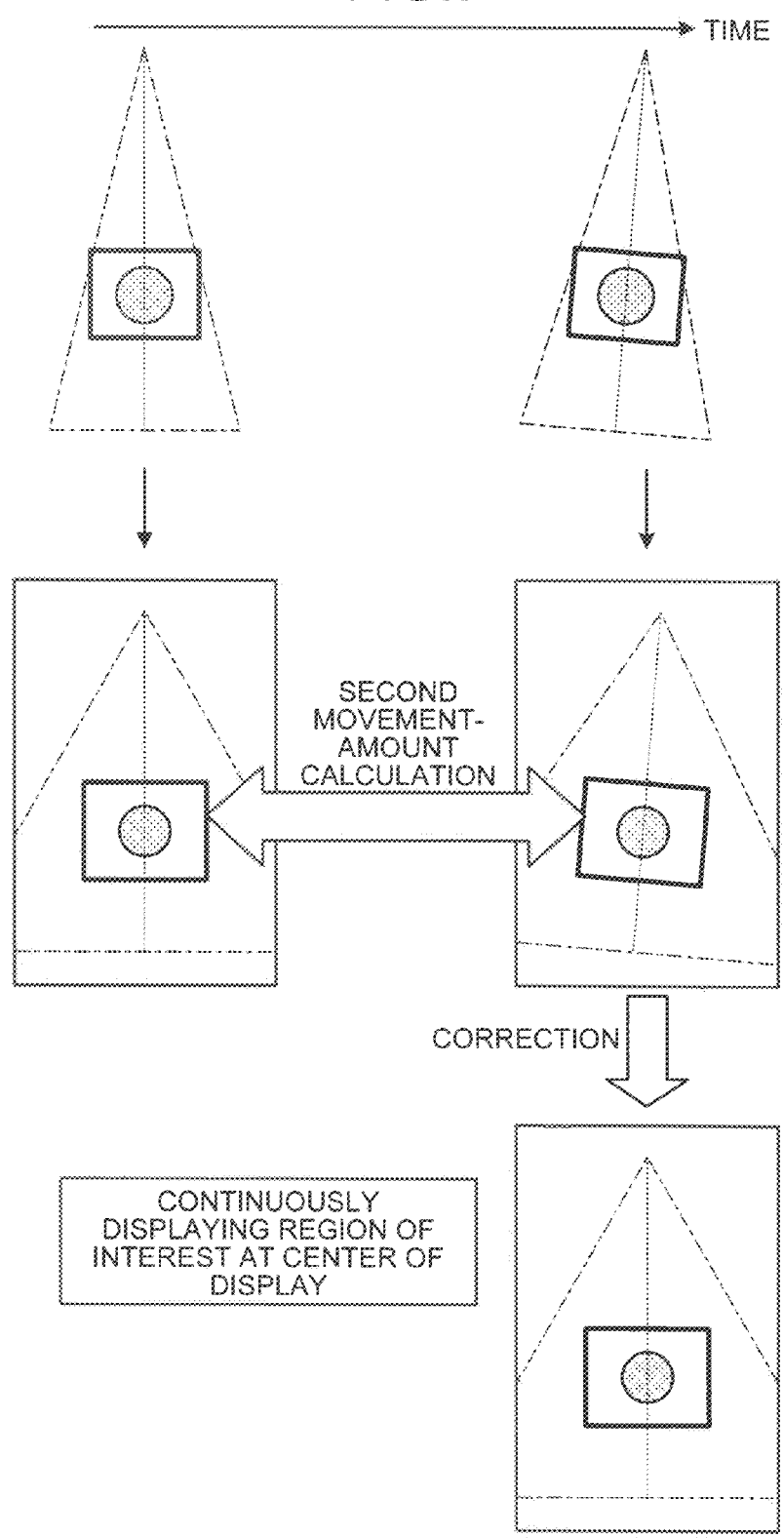
FIG. 7 is a schematic diagram for explaining a second movement-amount calculating unit and a display-position correcting unit.

Such main features are explained below with reference to FIGS. 2 to 7 as well as FIG. 1. FIG. 2 is a schematic diagram for explaining a region-of-interest display setting unit; FIG. 3 is a schematic diagram for explaining a first scan sequence; FIG. 4 is a schematic diagram for explaining a second scan sequence; FIG. 5 is a schematic diagram for explaining a third scan sequence; FIG. 6 is a schematic diagram for explaining a transmission-reception delay-amount computing unit and a computation/control circuit; and FIG. 7 is a schematic diagram for explaining a second movement-amount calculating unit and a display-position correcting unit.

The following description mainly explains a case where a liver is the diagnosis subject, and a tumor in the liver of a subject is the region of interest. Moreover, the following description explains a case where under a state in which the ultrasonic probe 1 is in contact with an abdomen of the subject, a two-dimensional ultrasonic beam is transmitted into the body of the subject; the B-mode processing unit 12 creates volume data for B-mode image composition from a received three-dimensional reception signal in accordance with a setting request from an operator of the ultrasonic diagnostic apparatus; the image creating circuit 14 creates respective B-mode images corresponding to two orthogonal cross sections; and the monitor 2 displays the two B-mode images. Hereinafter, the respective B-mode images corresponding to the orthogonal two cross sections are referred to as "a first display cross section" and "a second display cross section".

After an ultrasonic beam is generated, when the operator of the ultrasonic diagnostic apparatus presses "a tracking setting switch" included in the input device 3, the region-of-interest display setting unit 16a sets a region of interest to be included in an ultrasound image.

Specifically, to begin with, in accordance with the control by the computation/control circuit 15 that detects that "the tracking setting switch" is pressed, the region-of-interest display setting unit 16a combines a lined area for specifying a region of interest to be a tracking subject in the liver to be a diagnosis subject with "the first display cross section" and "the second display cross section" via the image creating circuit 14, and displays the combined image on the monitor 2.

For example, as shown in section (A) in FIG. 2, the region-of-interest display setting unit 16a combines a lined area display for setting a region of interest in a rectangle with "the first display cross section" and "the second display cross section" via the image creating circuit 14, and displays the combined image on the monitor 2 in a superposed manner. The lined area of a rectangle to be displayed in a superposed manner is initially set to be combined at the center of each of "the first display cross section" and "the second display cross section" to be displayed on the monitor 2; and the operator determines whether the region of interest is totally included in the displayed lined area, and whether the region of interest is positioned at the center of the displayed lined area by referring to the lined area of a rectangle displayed on the monitor 2.

If the region of interest is totally included in the displayed lined area, and furthermore, the region of interest is positioned at the center of the displayed lined area; as the operator of the ultrasonic diagnostic apparatus presses "a setting confirmation switch" included in the input device 3, the region-of-interest display setting unit 16a sets a region of interest to the region of the lined area displayed in a superposed manner according to the initial setting.

By contrast, if the region of interest is not totally included in the displayed lined area, or if the region of interest is not positioned at the center of the displayed lined area; the operator of the ultrasonic diagnostic apparatus adjusts the region of the lined area displayed in a superposed manner so as to be matched with the region of interest by moving, enlarging, or reducing the rectangle of the lined area by using "a track ball" included in the input device 3. As the operator of the ultrasonic diagnostic apparatus then presses "the setting confirmation switch" included in the input device 3, the region-of-interest display setting unit 16a sets a region of interest to the adjusted line area. The region-of-interest display setting unit 16a corresponds to "a region-of-interest setting unit" described in the claims.

The region-of-interest display setting unit 16a sets three-dimensional regional information in three-dimensional volume data to positional information about the respective regions of interest set on "the first display cross section" and "the second display cross section", as shown in section (A) in FIG. 2.

Although the first embodiment is explained above in the case of setting a region of interest in a rectangle, the present invention is not limited to this. For example, as shown in section (B) in FIG. 2, a region of interest can be set in a trapezoid along a scan line on "the first display cross section" and "the second display cross section". In such case, the region-of-interest display setting unit 16a sets positional information about regions of interest respectively set on "the first display cross section" and "the second display cross section" as three-dimensional regional information as shown on the right side of section (B) in FIG. 2.

Moreover, according to the first embodiment, explained above is a case of setting a region of interest based on a lined area that is displayed in a superposed manner in accordance with an initial setting; however, the present invention is not limited to this, and can be applied to a case where the operator sets a region of interest with such as a mouse included in the input device 3, by referring to "the first display cross section" and "the second display cross section" displayed on the monitor 2, and the region-of-interest display setting unit 16a sets positional information about the set region of interest as three-dimensional regional information.

When the operator of the ultrasonic diagnostic apparatus presses "start of tracking scan" included in the input device 3, the first movement-amount calculating unit 16b sequentially calculates a movement amount of the region of interest set by the region-of-interest display setting unit 16a between reception data along a time sequence, as a first movement amount. The first movement-amount calculating unit 16b corresponds to "an inter-reception-data movement-amount calculating unit" described in the claims; likewise, a first movement amount corresponds to "an inter-reception-data movement amount".

The first movement-amount calculating unit 16b calculates a first movement amount in accordance with one of a first condition, a second condition, and a third condition. The first condition is configured to use "reception data corresponding to an ultrasonic beam transmitted for calculating a first movement amount". The second condition is configured to use "reception data corresponding to an ultrasonic beam transmitted for calculating a first movement amount and reception data corresponding to an ultrasonic beam transmitted for creating an ultrasound image to be displayed on the monitor 2". The third condition is configured to use "reception data corresponding to an ultrasonic beam transmitted for creating an ultrasound image to be displayed on the monitor 2".

Selection of the first, second, or third condition is determined by the operator by using a touch command screen included in the input device 3. The scan-sequence storage unit 17b stores a first scan sequence for executing the first condition, a second scan sequence for executing the second condition, and a third scan sequence for executing the third condition. The calculation/control circuit 15 reads a scan sequence corresponding to a selected condition from the scan-sequence storage unit 17b, controls processing of generating a high voltage pulse and processing of creating reception data, both of which are performed by the transmitting-receiving unit 11, in accordance with the read scan sequence; and further controls a calculation such that the first movement-amount calculating unit 16b calculates a first movement amount from the reception data created by the transmitting-receiving unit 11. The first, second, and third scan sequences are explained below in order with reference to FIGS. 3, 4, and 5, respectively.

As shown in FIG. 3, the first scan sequence repeats alternately two-cross-section scans for calculating a first movement amount, and three-dimensional scans (hereinafter, "3D scan") for display for creating an ultrasound image (B-mode image) to be displayed on the monitor 2. According to the first embodiment, explained below is a case where scan regions of an ultrasonic beam transmitted from the ultrasonic probe 1 in a two-cross-section scan are two two-dimensional cross-sectional regions orthogonal to each other, each of the cross-sectional directions of the two is the same direction as each of the cross-sectional directions of "the first display cross section" and "the second display cross section".

Reception data created by the transmitting-receiving unit 11 through a two-cross-section scan of the first time in the first scan sequence is stored in the memory 18. After the two-cross-section scan of the first time, a 3D scan of the first time is then performed after a certain lapse. A reception signal received by the ultrasonic probe 1 through the 3D scan of the first time is processed through signal processing performed by the transmitting-receiving unit 11 (reception data creation processing), and image processing and display processing performed by the image creating circuit 14.

Reception data created by the transmitting-receiving unit 11 through a two-cross-section scan of the second time in the first scan sequence is then also stored in the memory 18, and the first movement-amount calculating unit 16b reads from the memory 18 the reception data according to the two-cross-section scan of the first time and the reception data according to the two-cross-section scan of the second time, and calculates a first movement amount.

Specifically, the first movement-amount calculating unit 16b calculates the amount of displacement of the region of interest in each reception data corresponding to "the first display cross section" among the reception data according to the two-cross-section scans of the first time and the second time, and the amount of displacement of the region of interest in each reception data corresponding to "the second display cross section" among the reception data according to the two-cross-section scans of the first time and the second time, through general computation processing, such as cross correlation processing or center-of-gravity computation; and calculates a first movement amount of the region of interest in three dimensions from each calculated amount of displacement with respect to each of the two orthogonal cross sections.

The first scan sequence is set such that start intervals of two-cross-section scans and start intervals of 3D scans are to be the same time length, so that the calculated amount of displacement is directly used as a first movement amount, as shown in FIG. 3.

After the two-cross-section scan of the second time, a 3D scan of the second time is then performed after a certain lapse, and a reception signal received by the ultrasonic probe through the 3D scan of the second time is also processed through the signal processing, the image processing, and the display processing, as shown in FIG. 3.

A two-cross-section scan of the third time is then performed in the first scan sequence; reception data created by the transmitting-receiving unit 11 through the two-cross-section scan of the third time is also stored in the memory 18, and the first movement-amount calculating unit 16b reads from the memory 18 the reception data according to the two-cross-section scan of the second time and the reception data according to the two-cross-section scan of the third time, and calculates a first movement amount. When the reception data created through the two-cross-section scan of the third time is stored in the memory 18, the reception data created through the two-cross-section scan of the first time is discarded.

After that, a 3D scan of the third time is performed, and a reception signal received by the ultrasonic probe through the 3D scan of the third time is processed through the signal processing, the image processing, and the display processing, as shown in FIG. 3.

Further subsequent processes are not shown in the figure, a two-cross-section scan of the fourth time and a 3D scan of the fourth time are sequentially performed; reception data created by the transmitting-receiving unit 11 through the two-cross-section scan of the fourth time is also stored in the memory 18, and the first movement-amount calculating unit 16b reads from the memory 18 the reception data according to the two-cross-section scan of the third time and the reception data according to the two-cross-section scan of the fourth time, and calculates a first movement amount. When the reception data created through the two-cross-section scan of the fourth time is stored in the memory 18, the reception data created through the two-cross-section scan of the second time is discarded.

In this way, according to first scan sequence, the first movement-amount calculating unit 16b sequentially calculates first movement amounts from reception data created through two-cross-section scans along the time sequence.

Processes shown in FIG. 3, namely, "delay-amount computation for a 3D scan", "delay-amount computation for a two-cross-section scan", and "the image processing and the display processing" for the 3D scan of the second time and the 3D scan of the third time will be explained later in explanations of the transmission-reception delay-amount computing unit 16c, the second movement-amount calculating unit 16d, and the display-position correcting unit 16e.

Although similarly to the first scan sequence, the second scan sequence repeats two-cross-section scans and 3D scans alternately; a calculation of a first movement amount uses reception data of a two-cross-section scan and reception data of a 3D scan as shown in FIG. 4.

According to the second scan sequence, after a 3D scan of the first time is performed, a two-cross-section scan of the first time is performed. Although similarly to the first scan sequence, a reception signal received through the 3D scan of the first time is processed through the signal processing performed by the transmitting-receiving unit 11 (reception data creation processing), and the image processing and the display processing performed by the image creating circuit 14; respective two-dimensional reception data corresponding to "the first display cross section" and "the second display cross section" from among part of three-dimensional reception data created by the transmitting-receiving unit 11 are stored in the memory 18.

Reception data created by the transmitting-receiving unit 11 through a two-cross-section scan of the first time in the second scan sequence is then also stored in the memory 18, and the first movement-amount calculating unit 16b reads from the memory 18 the reception data according to the 3D scan of the first time and the reception data according to the two-cross-section scan of the first time, and calculates a first movement amount.

Specifically, the first movement-amount calculating unit 16b calculates the amount of displacement of the region of interest in each reception data corresponding to "the first display cross section" among the reception data according to the 3D scan of the first time and the two-cross-section scan of the first time, and the amount of displacement of the region of interest in each reception data corresponding to "the second display cross section" among the reception data according to the 3D scan of the first time and the two-cross-section scan of the first time, through general computation processing, such as cross correlation processing or center-of-gravity computation.

As shown in FIG. 4, the amount of displacement calculated with respect to each of the two cross sections is movement information about the region of interest from a time point during the execution of a 3D scan until the execution of a two-cross-section scan, so that the first movement-amount calculating unit 16b calculates the amount of displacement per unit of time (speed) from the calculated amount of displacement. The first movement-amount calculating unit 16b then estimates the amount of displacement of the region of interest with respect to each of the two cross sections from the start of the previous (first-time) 3D scan until the start of the next (second-time) 3D scan, by calculating the sum of the calculated "amount of displacement" and the value of product of "a calculated speed" and "a time length from the termination of a two-cross-section scan until the start of a next 3D scan"; and calculates a first movement amount of the region of interest in three dimensions from the estimated amount of displacement with respect to each of the two orthogonal cross sections.

A reception signal received through a 3D scan of the second time in the second scan sequence is then also processed through the signal processing, the image processing and the display processing; and two-dimensional reception data corresponding to "the first display cross section" and "the second display cross section" from among part of three-dimensional reception data created by the transmitting-receiving unit 11 through the 3D scan of the second time is stored in the memory 18. After that, reception data created by the transmitting-receiving unit 11 through a two-cross-section scan of the second time is also stored in the memory 18; the first movement-amount calculating unit 16b reads the reception data according to the 3D scan of the second time and the reception data according to the two-cross-section scan of the second time from the memory 18, and calculates a first movement amount. When reading and calculating, reception data previously used for calculating the first movement amount is discarded.

After the two-cross-section scan of the second time, a 3D scan of the third time is performed after a certain lapse, then a reception signal received by the ultrasonic probe through the 3D scan of the third time is also processed through the signal processing, the image processing, and the display processing, as shown in FIG. 4; respective two-dimensional reception data corresponding to "the first display cross section" and "the second display cross section" from among part of three-dimensional reception data created by the transmitting-receiving unit 11 through the 3D scan of the third time are stored in the memory 18.

In this way, according to the second scan sequence, the first movement-amount calculating unit 16b sequentially calculates first movement amounts by using part of reception data created through 3D scans along the time sequence and reception data created through two-cross-section scans along the time sequence.

The processes shown in FIG. 4, namely, "the delay-amount computation for a 3D scan", "the delay-amount computation for a two-cross-section scan", and "the image processing and the display processing" for the 3D scan of the second time and the 3D scan of the third time will be explained later in explanations of the transmission-reception delay-amount computing unit 16c, the second movement-amount calculating unit 16d, and the display-position correcting unit 16e.

Differently from the first and the second scan sequences, the third scan sequence performs only 3D scans; as shown in FIG. 5, a calculation of a first movement amount uses only reception data of the 3D scans.

According to the third scan sequence, reception signals received through 3D scans of the first time and the second time are processed through the signal processing performed by the transmitting-receiving unit 11 (reception data creation processing), and the image processing and the display processing performed by the image creating circuit 14, similarly to the first and the second scan sequences.

As described above, reception data created by the transmitting-receiving unit 11 is stored in the memory 18, and the first movement-amount calculating unit 16b reads from the memory 18 part of three-dimensional reception data according to the 3D scan of the first time and part of three-dimensional reception data according to the 3D scan of the second time, and calculates a first movement amount.

Specifically, the first movement-amount calculating unit 16b calculates the amount of displacement of the region of interest in three dimensions in part of the reception data according to the 3D scan of the first time, and part of reception data according to the 3D scan of the second time, through general computation processing, such as cross correlation processing or center-of-gravity computation.

As shown in FIG. 5, the calculated amount of displacement in three dimensions is movement information about the region of interest from a time point during the execution of the previous (first-time) 3D scan until a time point during the executing of the latest (second-time) 3D scan, so that the first movement-amount calculating unit 16b calculates the amount of displacement per unit of time (speed) from the calculated amount of displacement in three dimensions. The first movement-amount calculating unit 16b then calculates a first movement amount of the region of interest in three dimensions from the start of "the latest (second-time) 3D scan until the start of the next (third-time) 3D scan", by calculating the sum of the calculated "amount of displacement" and 'the product of "a calculated speed" and "a time length from a time-point corresponding to the final piece of data used for the first movement-amount calculation until the start of the next 3D scan"'.

A reception signal received through a 3D scan of the third time in the third scan sequence is then also processed through the signal processing, the image processing and the display processing; and the first movement-amount calculating unit 16b reads part of the three-dimensional reception data according to the 3D scan of the second time and part of the three-dimensional reception data according to the 3D scan of the third time from the memory 18, and calculates a first movement amount.

The processes shown in FIG. 5, namely, "the delay-amount computation for a 3D scan", and "the image processing and the display processing" for the 3D scan of the second time and the 3D scan of the third time will be explained later in explanations of the transmission-reception delay-amount computing unit 16c, the second movement-amount calculating unit 16d, and the display-position correcting unit 16e.

Reception data subject to the first movement-amount calculation processing by the first movement-amount calculating unit 16b in the first, the second, and the third scan sequences described above can be all of the created data; however, to speed up a throughput, it is desirable that the first movement-amount calculating unit 16b performs the first movement-amount calculation processing on part of the reception data that includes a region of interest set by the region-of-interest display setting unit 16a.

Moreover, to speed up further the speed of the first movement-amount calculation processing, processing of degrading to lower bit, thinning of scan lines, processing of thinning sample points per scan line, and the like, can be performed on part of reception data that includes a region of interest. Furthermore, to speed up further the speed of the first movement-amount calculation processing, a feature amount of reception data is extracted, and then a first movement amount can be calculated between reception data by using the extracted feature amount. As a concrete method of extracting a feature amount of reception data, processing using a non-liner filter, such as an edge-enhancing filter, can be used.

Respective characteristics of the first, the second, and the third scan sequences are explained below. Because a two-cross-section scan dedicated for the first movement-amount calculation executed in the first and the second scan sequences is a cross-section scan, a scan time required for the two-cross-section scan can be shorter than a time required for a 3D scan. Accordingly, when a movement region of a region of interest is wide, a first movement amount can be securely calculated by ensuring that a scan region includes the region of interest by setting the scan region of a two-cross-section scan to a region extended from a scan region in cross-sectional directions corresponding in a 3D scan for display.

Moreover, according to the second scan sequence, by using reception data of a 3D scan, more accurate movement information about a region of interest between close time points is acquired, and the accuracy of a calculated first movement amount can be improved, compared with the first scan sequence.

Furthermore, according to the third scan sequence, the amount of displacement of a region of interest is calculated by using three-dimensional reception data differently from the first and the second scan sequences, so that even when a movement region of the region of interest is wide, a scan region includes the region of interest more securely than that in a cross-section scan, and a first movement amount can be more securely calculated.

Although the first embodiment is explained below in a case where the first movement-amount calculating unit 16b calculates a first movement amount of the region of interest from reception data actually acquired from tissue of a subject, the present invention is not limited to this. For example, it can be a case where information about amounts of temporal displacement of a tissue (for example, a liver) of the subject due to the breaths and the heart beats is stored in advance; cyclical movement of the tissue (cyclical information) is estimated by statistically processing the stored information; and then a first movement amount is calculated from the estimated cyclical information. Moreover, it can be a case of calculating a first movement amount by combining estimated cyclical information and reception data actually acquired from a tissue of the subject.

Returning to FIG. 1, based on a first movement amount sequentially calculated by the first movement-amount calculating unit 16b, the transmission-reception delay-amount computing unit 16c computes a delay-time amount (hereinafter, "delay amount") for when generating a high voltage pulse by using a predetermined computation procedure stored by the setting-information storage unit 17 for sequentially shifting the scan region of an ultrasonic beam transmitted from the ultrasonic probe 1, and then the computation/control circuit 15 performs control such that a high voltage pulse is generated from the pulser built in the transmitting-receiving unit 11, based on the delay amount obtained by the computation processing performed by the transmission-reception delay-amount computing unit 16c. The transmission-reception delay-amount computing unit 16c and the computation/control circuit 15 correspond to "a scan-region control unit" described in the claims.

In other words, when the region of interest moves, if the ultrasonic probe 1 in contact with an abdomen of the subject is fixed without being moved by the operator, as shown in section (A) in FIG. 6, the scan region of an ultrasonic beam transmitted from the ultrasonic probe 1 is fixed in a 3D scan for display, consequently, the region of interest moves inside of a lined area set by the region-of-interest display setting unit 16a on the first display cross section and the second display cross section. Moreover, when the region of interest moves to a large extent, the region of interest is deviated from the lined area set by the region-of-interest display setting unit 16a on the first display cross section and the second display cross section.

However, according to the delay-amount calculation processing by the transmission-reception delay-amount computing unit 16c and high-voltage generation control processing by the computation/control circuit 15, as shown in section (B) in FIG. 6, a scan region of an ultrasonic beam can be moved by tracking correspondingly to a movement of the region of interest, as a result, the relative position of the region of interest inside the lined area set by the region-of-interest display setting unit 16a can be consistent on the first display cross section and the second display cross section.

When the first condition or the second condition is selected by the operator, and processing is performed in accordance with the first scan sequence or the second scan sequence, the scan region of an ultrasonic beam is shifted also in a two-cross-section scan through the delay-amount calculation processing by the transmission-reception delay-amount computing unit 16c and the high-voltage generation control processing by the computation/control circuit 15, based on first movement amounts sequentially calculated by the first movement-amount calculating unit 16b.

The term "delay-amount computation for a 3D scan" shown in FIGS. 3, 4, and 5, and the term "delay-amount computation for a two-cross-section scan" shown in FIGS. 3 and 4 correspond to the above-described processing performed by the transmission-reception delay-amount computing unit 16c and the computation/control circuit 15.

The computation/control circuit 15 then performs control such that the focus point of an ultrasonic beam to be transmitted from the ultrasonic probe 1 is sequentially moved along with a shift of the scan region, based on a first movement amount sequentially calculated by the first movement-amount calculating unit 16b.

In other words, at the time when a region of interest is set in a lined area by the region-of-interest display setting unit 16a, the computation/control circuit 15 controls the generation of a high voltage pulse by the transmitting-receiving unit 11 such that a focus point of an ultrasonic beam to be transmitted from the ultrasonic probe 1 into the subject comes close to the set region of interest in a 3D scan; and each time when a first movement amount is calculated by the first movement-amount calculating unit 16b, as shown in section (B) in FIG. 6, the computation/control circuit 15 controls the transmitting-receiving unit 11 so as to move the focus point in a tracking manner, by tracking the movement of the region of interest, along with tracking movement of the scan region.

Returning to FIG. 1, the B-mode processing unit 12 creates data for two-dimensional B-mode image composition along the time sequence (hereinafter, "image data") based on reception data corresponding an ultrasonic beam transmitted to the scan region that is sequentially shifted through the delay-amount computation processing performed by the transmission-reception delay-amount computing unit 16c and the high-voltage pulse generation control processing performed by the computation/control circuit 15, and stores the created data in the memory 18. The second movement-amount calculating unit 16d then sequentially calculates a movement amount of the region of interest set by the region-of-interest display setting unit 16a between sequentially created image data along the time sequence as a second movement amount. The second movement-amount calculating unit 16d corresponds to "an inter-image movement-amount calculating unit" described in the claims; likewise, a second movement amount corresponds to "an inter-image movement amount".

Specifically, as shown in FIG. 7, the second movement-amount calculating unit 16d calculates a second movement amount through general computation processing, such as cross correlation processing or center-of-gravity computation similarly to the first movement-amount calculating unit 16b, between image data created by the B-mode processing unit 12 from the reception data created by the transmitting-receiving unit 11 correspondingly to an ultrasonic wave transmitted into the scan region that is shifted by tracking the region of interest.

Returning to FIG. 1, a conventional computation/control circuit performs control such that image data crated by the B-mode processing unit 12 is processed to an image by the image creating circuit 14, and then the image is displayed by the monitor 2. However, according to the present invention, the computation/control circuit 15 performs control such that the display-position correcting unit 16e shown in FIG. 1 corrects the region of interest included in image data sequentially created by the B-mode processing unit 12 based on the second movement amount sequentially calculated by the second movement-amount calculating unit 16d so as to be displayed at the same display position on the screen of the monitor 2, then the image creating circuit 14 creates an image from the corrected data, and then the monitor 2 displays the created image. The computation/control circuit 15 and the display-position correcting unit 16e correspond to "a display control unit" described in the claims.

In other words, as shown in FIG. 7, the display-position correcting unit 16e processes the image data created by the B-mode processing unit 12 through processing of correcting the display position by the second movement amount calculated by the second movement-amount calculating unit 16d, i.e., processing of returning the display position by the second movement amount, and then transmits image data to the image creating circuit 14. Accordingly, an error correction of the scan region caused by movement tracking control can be compensated, so that the region of interest can be continuously displayed at the center of the screen of the monitor 2.

The term "the image processing and the display processing" according to the 3D scan of the second time and the 3D scan of the third time shown in FIGS. 3, 4, and 5, corresponds to the above-described processing performed by the second movement-amount calculating unit 16d, the display-position correcting unit 16e, and the computation/control circuit 15.

Although the first embodiment is explained above in a case of calculating a second movement amount between two-dimensional image data for display along the time sequence created by the B-mode processing unit 12, the present invention is not limited to this, and can be applied to a case of calculating a second movement amount between two-dimensional image data for display along the time sequence created by the doppler processing unit 13. Moreover, it can be a case where a second movement amount is calculated between ultrasound images along the time sequence created by the image creating circuit 14, and then a created ultrasound image is corrected and displayed.

The above-described processing of tracking the movement of a region of interest is terminated when the operator presses "a tracking-scan termination switch" included in the input device 3.

Figure 8:
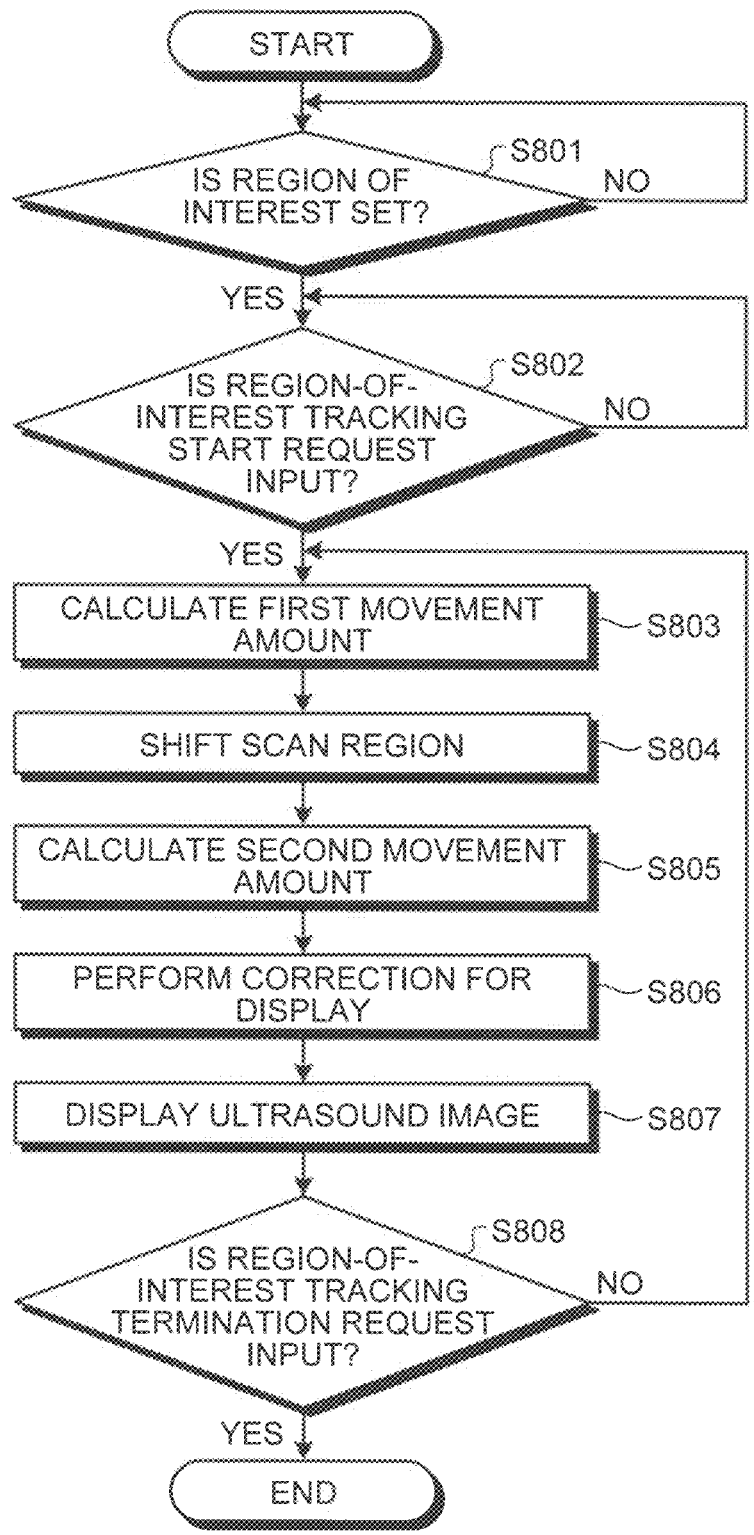
FIG. 8 is a flowchart for explaining processing by the ultrasonic diagnostic apparatus according to the first embodiment.

Processing by the ultrasonic diagnostic apparatus according to the first embodiment is explained below with reference to FIG. 8. FIG. 8 is a flowchart for explaining processing by the ultrasonic diagnostic apparatus according to the first embodiment.

As shown in FIG. 8, according to the ultrasonic diagnostic apparatus according to the first embodiment, when an operator who presses "the tracking setting switch" included in the input device 3 sets a region of interest by referring to an ultrasound image on which lined areas are displayed in a superposed manner on the monitor 2 in accordance with an instruction by the region-of-interest display setting unit 16a (Yes at Step S801), the ultrasonic diagnostic apparatus waits until a region-of-interest tracking start request is input as the operator presses "the tracking setting switch" included in the input device 3 (Step S802).

When a region-of-interest tracking start request is input (Yes at Step S802), the computation/control circuit 15 reads from the scan-sequence storage unit 17b a scan sequence corresponding to a selected condition that is input together with the region-of-interest tracking start request, corresponding to the first, the second, or the third scan sequence, and controls the high-voltage generation processing, the reception data creation corresponding, and the like performed by the transmitting-receiving unit 11. Accordingly, the first movement-amount calculating unit 16b calculates a first movement amount by using two pieces of reception data created and stored in the memory 18 by the transmitting-receiving unit 11 (Step S803).

Based on a first movement amount calculated by the first movement-amount calculating unit 16b, the transmission-reception delay-amount computing unit 16c then computes a delay amount for when generating a high voltage pulse by using a predetermined computation procedure stored by the setting-information storage unit 17, for shifting the scan region of an ultrasonic beam to be transmitted from the ultrasonic probe 1; and then the computation/control circuit 15 performs control such that a high voltage pulse is generated from the pulser built in the transmitting-receiving unit 11, based on the delay amount obtained by the computation processing performed by the transmission-reception delay-amount computing unit 16c, thereby shifting the scan region (Step S804). At the same time, the focus point is also moved in a tracking manner.

After that, the second movement-amount calculating unit 16d calculates a movement amount of the region of interest set by the region-of-interest display setting unit 16a between image data along the time sequence, as a second movement amount (Step S805).

Subsequently, the display-position correcting unit 16e corrects the region of interest included in the image data so as to be displayed at the same display position on the screen of the monitor 2 based on the second movement amount calculated by the second movement-amount calculating unit 16d (Step S806); and the computation/control circuit 15 performs control such that the monitor 2 displays an ultrasound image created by the image creating circuit 14 based on correction processing performed by the display-position correcting unit 16e (Step S807).

The computation/control circuit 15 then determines whether "the tracking-scan termination switch" included in the input device 3 is pressed by the operator, i.e., whether a region-of-interest tracking termination request is input (Step S808). If region-of-interest tracking termination request is not input (No at Step S808), the process control goes back to Step S803, and performs the processing of tracking the region of interest by using a latest reception data.

On the contrary, if the region-of-interest tracking termination request is input (Yes at Step S808), the computation/control circuit 15 terminates the processing.

As described above, according to the first embodiment, the region-of-interest display setting unit 16a sets a region of interest to be included in an ultrasound image. The first movement-amount calculating unit 16b sequentially calculates a movement amount of the region of interest set by the region-of-interest display setting unit 16a between reception data along the time sequence as a first movement amount. Based on a first movement amount sequentially calculated by the first movement-amount calculating unit 16b, the transmission-reception delay-amount computing unit 16c computes a delay amount for when generating a high voltage pulse, for sequentially shifting the scan region of an ultrasonic beam, and then the computation/control circuit 15 performs control such that a high voltage pulse is generated based on the delay amount obtained by the computation processing performed by the transmission-reception delay-amount computing unit 16c. Accordingly, a scan area of an ultrasonic beam, set as narrow as possible to achieve both a certain image quality and realtime responsiveness of an ultrasound image, can be dynamically moved to ensure that a region of interest is to be included within the scan region. As a result, the subject does not need "to hold the breath", and the operator can execute a scan for an ultrasound image while fixing the ultrasonic probe 1. Therefore, a stress on the subject and a burden on the operator can be reduced while maintaining the image quality and the responsiveness of an ultrasound image when a region of interest moves, as described main features above. Because the region of interest does not deviate from an ultrasound image to be displayed, a possibility of performing another scan for an ultrasound image can be reduced, and efficiency in diagnosis can be improved.

Moreover, according to the first embodiment, the second movement-amount calculating unit 16d sequentially calculates a movement amount of the region of interest set by the region-of-interest display setting unit 16a between sequentially created image data along the time sequence, as a second movement amount. The display-position correcting unit 16e corrects a display position based on the second movement amount sequentially calculated by the second movement-amount calculating unit 16d such that the region of interest included in the image data sequentially created by the B-mode processing unit 12 is to be displayed at the same display position on the screen of the monitor 2; and the computation/control circuit 15 performs control such the image creating circuit 14 creates an image from the image data in which the display position is corrected by the display-position correcting unit 16e, and then the monitor 2 displays the created image. Accordingly, the region of interest can be constantly displayed at a fixed position on an image, and a diagnosis can be more easily conducted by a doctor who reads ultrasound images along the time sequence.

Furthermore, according to the first embodiment, the computation/control circuit 15 performs control such that the focus point of an ultrasonic beam to be transmitted from the ultrasonic probe 1 is sequentially moved along with a shift of the scan region based on a first movement amount sequentially calculated by the first movement-amount calculating unit 16b. Accordingly, the image quality of an ultrasound image can be constantly maintained at a satisfactory condition, so that a diagnosis can be more easily conducted by a doctor who reads ultrasound images along the time sequence.

Figure 9:
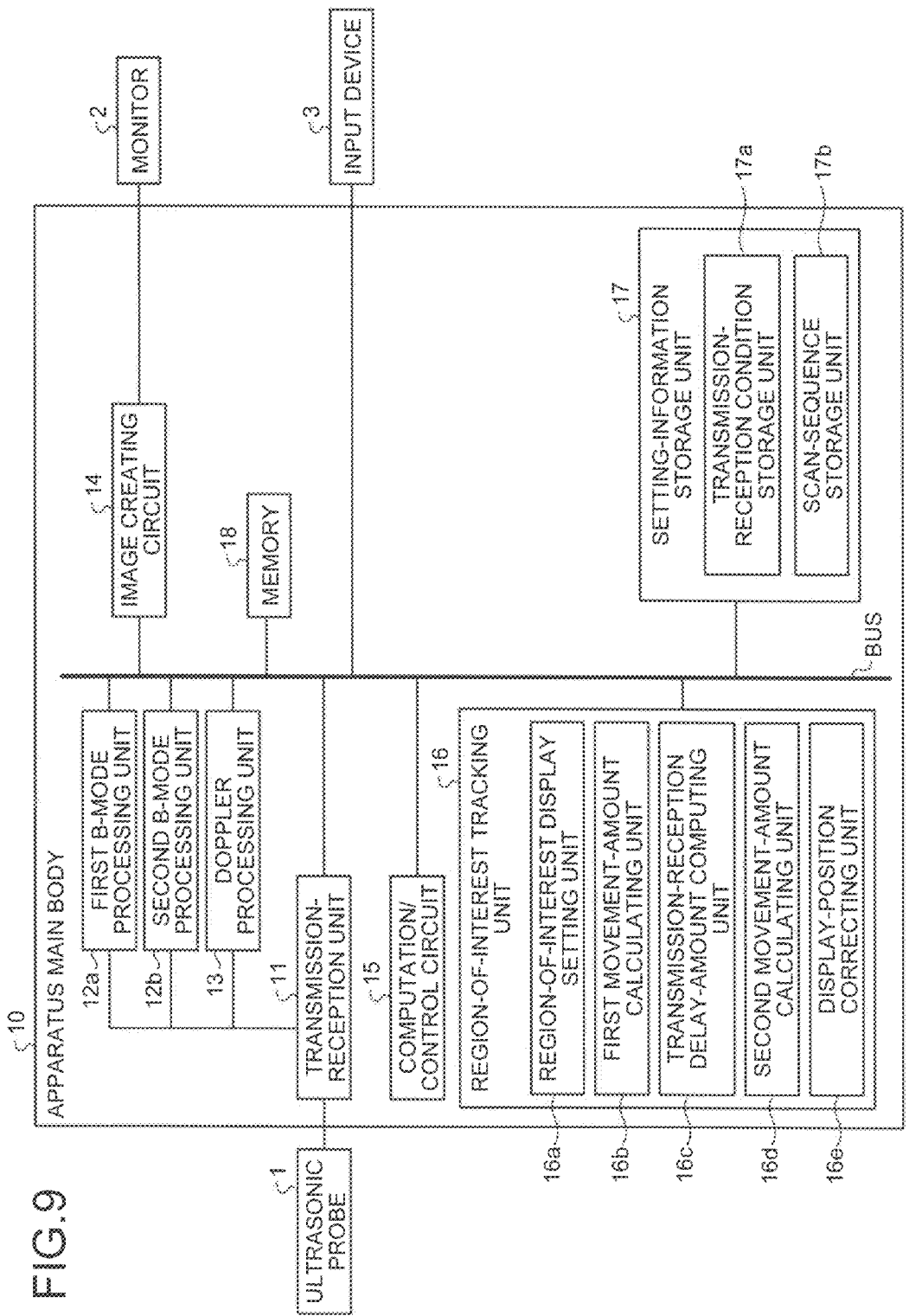
FIG. 9 is a schematic diagram for explaining of a configuration of an ultrasonic diagnostic apparatus according to a second embodiment of the present invention.
Figure 10:
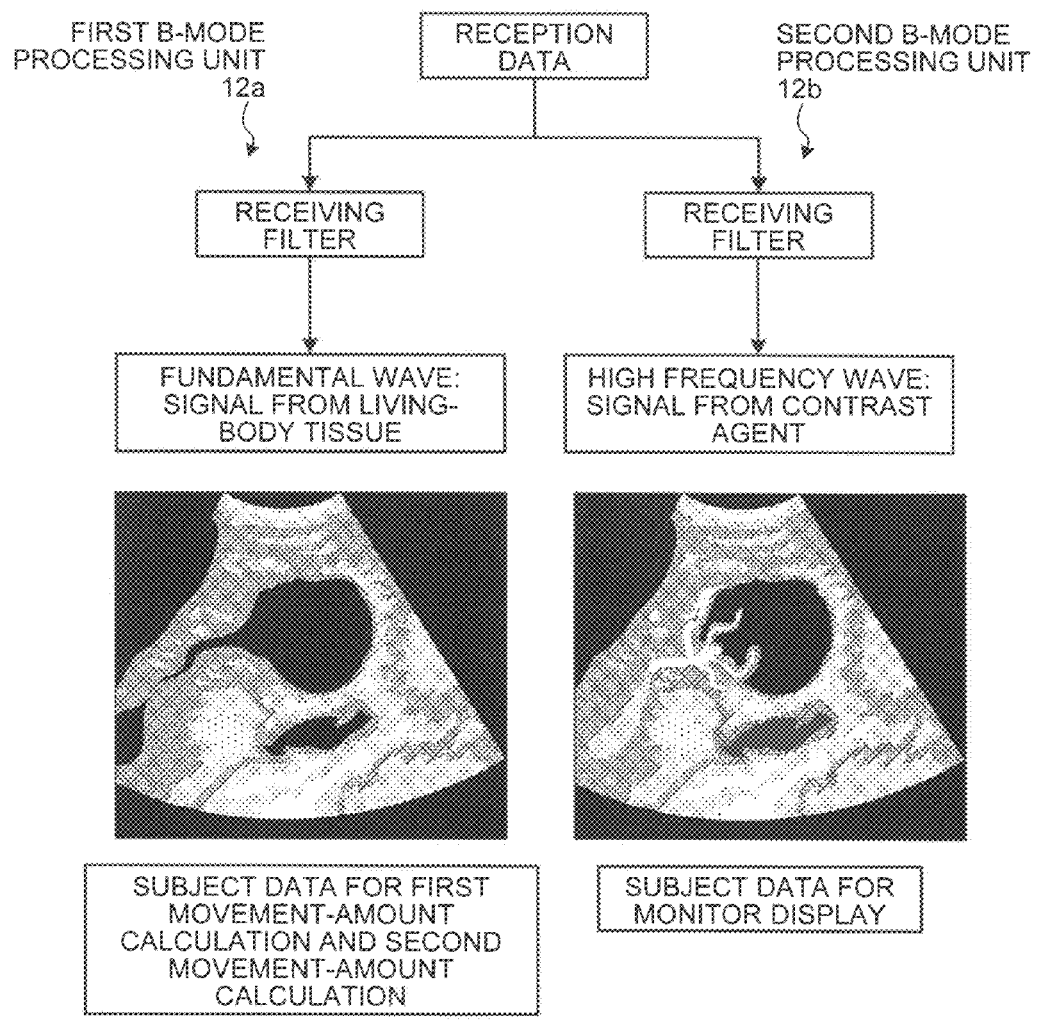
FIG. 10 is a schematic diagram for explaining a feature of the ultrasonic diagnostic apparatus according to the second embodiment.

A second embodiment of the present invention is explained below in a case of tracking a region of interest when displaying an ultrasound image of a subject into which a contrast agent is injected, with reference to FIGS. 9 and 10. FIG. 9 is a schematic diagram for explaining of a configuration of an ultrasonic diagnostic apparatus according to the second embodiment; and FIG. 10 is a schematic diagram for explaining a feature of the ultrasonic diagnostic apparatus according to the second embodiment.

The ultrasonic diagnostic apparatus according to the second embodiment has a configuration substantially similar to the ultrasonic diagnostic apparatus according to the first embodiment; however, as shown in FIG. 9, it is different from the first embodiment in the point that the B-mode processing unit 12 is separated into two systems, namely, a first B-mode processing unit 12a and a second B-mode processing unit 12b. The following description mainly explains the B-mode processing units.

There is an examination method of contrast imaging of confirming a state of the inflow of blood, the architecture of blood vessels, and volume of blood flows with a contrast agent for determining benignancy or malignancy of a tumor. An examination with a contrast agent is performed also in diagnostic imaging by an ultrasonic diagnostic apparatus similarly to diagnostic imaging by an X-ray diagnostic apparatus, an X-ray Computed Tomography (CT) apparatus, or a Magnetic Resonance Imaging (MRI) apparatus. However, a contrast agent used by ultrasonic diagnostic apparatuses is not a liquid but microbubbles, different from the other medical diagnostic imaging apparatuses.

For this reason, two typical methods of acquiring a contrast signal that uses characteristics unique to bubbles are available for ultrasonic diagnostic apparatuses. One of the two methods is creating an image on which "a region filled with a contrast agent" is continuously being clarified by obtaining a strong signal by vibrating microbubbles of the contrast agent as the target with a relatively low sound pressure and causing a strong signal by resonance of the vibration. The other method is creating an image on which "a region filled with a contrast agent" is clarified by obtaining a strong signal each time when a microbubble is broken by breaking microbubbles with a transmission of a high sound pressure. According to the both methods, in accordance with physical characteristics of a contrast agent to be used, a creation of an image on which a signal from the contrast agent is highlighted is usually performed by extracting a subharmonic wave or a higher harmonic wave with which a difference between a signal from the contrast agent and a signal form a living body tissue becomes large through frequency filtering, and by using an extracted subharmonic wave or an extracted high frequency wave.

Across images along the time sequence that are displayed by extracting a signal from the contrast agent, the state of blood-flow distributions changes every minute depending on a situation the contrast agent is spread. The ultrasonic diagnostic apparatus according to the first embodiment can correct a relative positional deviation between reception data and a relative positional deviation between data for image composition caused by movement of the region of interest, by creating reception data by the transmitting-receiving unit 11 with the use of a reception signal in a subharmonic wave or a high frequency wave and then calculating a first movement amount, and creating data for image composition by the B-mode processing unit 12 or the doppler processing unit 13 and then calculating a second movement amount.

However, such effect is produced only when executing a sufficiently high scan rate, or when the inflow of a blood flow is slow; consequently, if signals from the contrast agent change dynamically, for example, when the inflow of a blood flow is fast, there is a possibility that tracking of movement of the region of interest cannot be accurately executed.

As described above, to obtain a resonance frequency of a contrast agent or a signal at destruction efficiently, a signal according to the contrast agent is obtained by extracting through frequency filtering a subharmonic wave or a higher harmonic wave with which a difference between a signal from the contrast agent and a signal from a living body tissue becomes large. A signal from a living body tissue not from the contrast agent is at the fundamental wave frequency equal to a transmission frequency, and strong. Even if injecting the contrast agent, a living body tissue itself does not change, so that an image that is not influenced by a signal from the contrast agent, i.e., an image of only living body tissue, can be created by using the fundamental wave.

According to the second embodiment, processing of creating data for B-mode image composition is performed in a separated manner by two systems, namely, the first B-mode processing unit 12a and the second B-mode processing unit 12b.

In other words, the first B-mode processing unit 12a includes a filter that separates a fundamental wave for extracting data dominated by living-body tissue signals from reception data created by the transmitting-receiving unit 11; and the second B-mode processing unit 12b includes a filter that separates a subharmonic wave or a higher harmonic wave for extracting data dominated by contrast agent signals from reception data created by the transmitting-receiving unit 11.

As shown in FIG. 10, the first B-mode processing unit 12a extracts a fundamental wave that is a signal from a living body tissue through a receiving filter included in the first B-mode processing unit 12a, and creates data for B-mode image composition from the extracted fundamental wave. The fundamental wave and the data for B-mode image composition acquired by the first B-mode processing unit 12a become subject data for a first movement-amount calculation and a second movement-amount calculation, respectively.

Precisely, the first B-mode processing unit 12a extracts a fundamental wave that is a signal from a living body tissue through its own receiving filter; and the first movement-amount calculating unit 16b sequentially calculates a first movement amount by using the fundamental wave extracted by the first B-mode processing unit 12a. Accordingly, similarly to the first embodiment, the transmission-reception delay-amount computing unit 16c computes a delay amount based on the first movement amount, and the computation/control circuit 15 shifts a scan region based on the delay amount.

Furthermore, the first B-mode processing unit 12a creates data for B-mode image composition of only living body tissue from the extracted fundamental wave; and the second movement-amount calculating unit 16d calculates a second movement amount between the data for B-mode image composition along the time sequence created by the first B-mode processing unit 12a. Accordingly, similarly to the first embodiment, correction processing is performed by the display-position correcting unit 16e. Above-described "data for B-mode image composition of only living body tissue" corresponds to "a first ultrasound image" described in the claims.

As shown in FIG. 10, the second B-mode processing unit 12b extracts a high frequency wave that is a signal from the contrast agent through a receiving filter that the second B-mode processing unit 12b includes, and creates data for B-mode image composition in which "a region filled with the contrast agent" is highlighted. The data for B-mode image composition created by the second B-mode processing unit 12b then becomes monitor display data to be displayed on the monitor 2. Above-described "data for B-mode image composition in which a region filled with the contrast agent is highlighted" corresponds to "a second ultrasound image" described in the claims.

In other words, the display-position correcting unit 16e sequentially performs correction processing based on the second movement amount on data for B-mode image composition sequentially created by the second B-mode processing unit 12b, and the computation/control circuit 15 performs control such that the monitor 2 displays ultrasound images (contrast-agent highlighted B-mode images) sequentially created by the image creating circuit 14 based on the correction processing performed by the display-position correcting unit 16e.

Although the second embodiment is explained above in a case where the monitor 2 displays a contrast-agent highlighted B-mode image created by the image creating circuit 14 from data for B-mode image composition sequentially created by the second B-mode processing unit 12b, the present invention is not limited to this, and can be applied to a case where the monitor 2 displays a living-body tissue B-mode image created by the image creating circuit 14 from data for B-mode image composition created by the first B-mode processing unit 12a together with a contrast-agent highlighted B-mode image in parallel, or a case where the monitor 2 displays a contrast-agent highlighted B-mode image and a living-body tissue B-mode image in a superposed manner.

Moreover, it can be a case where the doppler processing unit 13 processes a signal from the contrast agent and creates data for doppler image composition that reflects information about the speed, the power, and the distribution of blood flows; the display-position correcting unit 16e performs correction processing on the created data; the image creating circuit 14 creates a doppler image from the corrected data; and then the monitor 2 displays the created doppler image. Furthermore, it can be a case where a doppler image is displayed by the monitor 2 in parallel with a contrast-agent highlighted B-mode image and/or a living-body tissue B-mode image.

Explanations of the processing by the ultrasonic diagnostic apparatus according to the second embodiment are omitted, because it is the same as the processing by the ultrasonic diagnostic apparatus according to the first embodiment explained with reference to FIG. 8, except that subject data for the first movement-amount calculation and the second movement-amount calculation are a fundamental wave extracted by the first B-mode processing unit 12a and data for B-mode image composition created from the fundamental wave.

As described above, according to the second embodiment, because a first movement amount and a second movement amount are calculated based on a fundamental wave that reflects only information about living body tissue, and then a scan region is shifted and corrected for display; even when signals from the contrast agent change dynamically, tracking of movement of the region of interest can be accurately executed. Therefore, when the region of interest moves in an contrast-imaging examination, a stress on a subject and a burden on an operator can be reduced while maintaining the image quality and realtime responsiveness of an ultrasound image.

Although the first embodiment is explained above in the case of executing two-cross-section scans in the first and the second scan sequences for calculating first movement amounts with respect to the same cross sections as those to be displayed on the monitor 2, the present invention is not limited to this. It can be a case of executing two-cross-section scans for calculating first movement amounts with respect to two cross sections in different directions from cross sections to be displayed on the monitor 2. Moreover, it can be a case of executing cross-section scans for calculating first movement amounts with respect to different cross sections in three or more directions.

Although the first and second embodiments are explained above in a case of tracking movement of a region of interest when scanning three-dimensionally with an ultrasonic beam by using a two-dimensional ultrasonic probe, the present invention is not limited to this. It can also be a case of tracking movement of a region of interest when scanning two-dimensionally with an ultrasonic beam by using a one-dimensional ultrasonic probe. In such case, the first movement-amount calculating unit 16b sequentially calculates a first movement amount by using reception data sequentially created through cross-section scans for display along the time sequence, and then a shift of an ultrasonic beam and a correction processing for display are performed by using the calculated first movement amount. Accordingly, when performing a cross-section scan, even if a region of interest moves, a stress on a subject and a burden on an operator can be reduced while maintaining the image quality and the realtime responsiveness of an ultrasound image.

The components of each device shown in the drawings are conceptual for describing functions, and not necessarily to be physically configured as shown in the drawings. In other words, concrete forms of distribution and integration of the units are not limited to those shown in the drawings, and all or part of the units can be configured to be functionally or physically distributed and integrated in an arbitrary unit depending on various loads and conditions in use. Furthermore, all or an arbitrary part of processing functions performed by the respective units can be implemented by a Central Processing Unit (CPU) and a computer program to be executed by the CPU, or can be implemented as hardware by wired logic.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnostic apparatus comprising:
an ultrasonic probe configured to send and receive ultrasonic waves;
a region-of-interest setting unit that sets a region of interest to be included in an ultrasound image created based on reception data acquired by using an ultrasonic wave reflected from a subject;
a receiving filter that separates a fundamental wave and one of a subharmonic wave and a higher harmonic wave from a same reception data;
an inter-reception-data movement-amount calculating unit that calculates a movement amount of the region of interest set by the region-of-interest setting unit between fundamental waves each of which is separated by the receiving filter from each of reception data acquired by using an ultrasonic wave reflected from the subject at different times, as an inter-reception-data movement amount;
a scan-region control unit that controls a scan region of an ultrasonic wave to be transmitted from the ultrasonic probe such that the scan region is to be shifted based on the inter-reception-data movement amount calculated by the inter-reception-data movement-amount calculating unit;
an image creating unit that creates a plurality of ultrasound images along a time sequence based on one of subharmonic waves along the time sequence and higher harmonic waves along the time sequence separated by the receiving filter from reception data corresponding to an ultrasonic wave transmitted from the ultrasonic probe into the scan region shifted according to control by the scan-region control unit; and
a display control unit that controls display of the ultrasound images along the time sequence created by the image creating unit on a predetermined display unit and controls display of the region of interest to remain at a same position on the predetermined display unit based upon the movement amount calculated by the inter-reception-data movement-amount calculating unit.

2. The apparatus according to claim 1, further comprising an inter-image movement-amount calculating unit that calculates a movement amount of the region of interest set by the region-of-interest setting unit between the ultrasound images along the time sequence created by the image creating unit as an inter-image movement amount, wherein the display control unit controls display of the region of interest included in each of the ultrasound images along the time sequence created by the image creating unit at a same display position on the predetermined display unit, based on the inter-image movement amount calculated by the inter-image movement-amount calculating unit.

3. The apparatus according to claim 2, wherein
each time when a new ultrasound image is created by the image creating unit, the inter-image movement-amount calculating unit calculates in real time an inter-image movement amount using created new ultrasound image, and
each time when a new inter-image movement amount is calculated by the inter-image movement-amount calculating unit, the display control unit controls display in real time of the region of interest to be included in the new ultrasound image created by the image creating unit at a same position on the predetermined display unit based on calculated new inter-image movement amount.

4. The apparatus according to claim 2, wherein
the image creating unit creates, along a time sequence, a first ultrasound image that is an ultrasound image based on the fundamental wave separated by the receiving filter, and a second ultrasound image that is an ultrasound image based on one of the subharmonic wave and the higher harmonic wave separated by the receiving filter, from reception data corresponding to an ultrasonic wave transmitted from the ultrasonic probe into the scan region shifted according to control by the scan-region control unit,
the inter-image movement-amount calculating unit calculates the inter-image movement amount between first ultrasound images created along the time sequence by the image creating unit, and
the display control unit controls display of the region of interest at a same position on the predetermined display unit based on the inter-image movement amount calculated by the inter-image movement-amount calculating unit in each of cases when displaying the second ultrasound image created by the image creating unit, when displaying the first ultrasound image and the second ultrasound image in parallel, and when displaying the first ultrasound image and the second ultrasound image in a superposed manner, on the predetermined display unit.

5. The apparatus according to claim 4, wherein
each time when a new fundamental wave is separated by the receiving filter, the inter-reception-data movement-amount calculating unit calculates in real time an inter-reception-data movement amount using separated new fundamental wave,
each time when a new inter-reception-data movement amount is calculated by the inter-reception-data movement-amount calculating unit, the scan-region control unit controls a scan region of an ultrasonic wave to be transmitted from the ultrasonic probe such that the scan region is to be shifted in real time based on calculated new inter-reception-data movement amount,
the image creating unit creates in real time a first ultrasound image and a second ultrasound image based on reception data corresponding to an ultrasonic wave transmitted from the ultrasonic probe into the scan region shifted according to control by the scan-region control unit,
each time when a new first ultrasound image and a new second ultrasound image are created by the image creating unit, the inter-image movement-amount calculating unit calculates an inter-image movement amount using created new first ultrasound image, and
each time when a new inter-image movement amount is calculated by the inter-image movement-amount calculating unit, the display control unit controls display in real time of the region of interest at a same display position on the predetermined display unit based on calculated new inter-image movement amount.

6. The apparatus according to claim 1, wherein the inter-reception-data movement-amount calculating unit uses at least one of reception data corresponding to an ultrasonic wave transmitted for calculating the inter-reception-data movement amount, and reception data corresponding to an ultrasonic wave transmitted for creating an ultrasound image displayed on the predetermined display unit.

7. The apparatus according to claim 1, wherein the scan-region control unit controls a scan region of an ultrasonic wave to be transmitted from the ultrasonic probe such that the scan region is to be shifted after moving a focus position of the ultrasonic wave to be transmitted from the ultrasonic probe, based on the inter-reception-data movement amount calculated by inter-reception-data movement-amount calculating unit.

8. The apparatus according to claim 1, wherein
each time when new reception data for calculating the inter-reception-data movement amount is acquired, the inter-reception-data movement-amount calculating unit calculates in real time an inter-reception-data movement amount using acquired new reception data,
each time when a new inter-reception-data movement amount is calculated by the inter-reception-data movement-amount calculating unit, the scan-region control unit controls a scan region of an ultrasonic wave to be transmitted from the ultrasonic probe such that the scan region is to be shifted in real time based on calculated new inter-reception-data movement amount,
the image creating unit creates in real time an ultrasound image based on reception data corresponding to an ultrasonic wave transmitted from the ultrasonic probe into the scan region shifted according to control by the scan-region control unit, and
each time when a new ultrasound image is created by the image creating unit, the display control unit controls display of created new ultrasound image on the predetermined display unit in real time.

9. The apparatus according to claim 1, wherein the fundamental waves are used for creating B-mode image data.

10. The apparatus according to claim 1, wherein the scan-region control unit controls a scan region of an ultrasonic wave to be transmitted from the ultrasonic probe such that the scan region is to be shifted after moving a focus position of the ultrasonic wave to be transmitted from the ultrasonic probe close to the region of interest, based on the inter-reception-data movement amount calculated by inter-reception-data movement-amount calculating unit, and the focus point is close to the region of interest.

11. A method of ultrasonic diagnosis, comprising:
transmitting an ultrasonic wave towards a subject;
setting a region of interest to be included in an ultrasound image created based on reception data acquired by using an ultrasonic wave reflected from the subject, by a region-of-interest setting unit;
separating a fundamental wave and one of a subharmonic wave and a higher harmonic wave from a same reception data, by a receiving filter;
calculating a movement amount of set region of interest between fundamental waves each of which is separated by the receiving filter from reception data acquired by using an ultrasonic wave reflected from the subject at different times, as an inter-reception-data movement amount, by an inter-reception-data movement-amount calculating unit;
controlling a scan region of an ultrasonic wave to be transmitted from an ultrasonic probe such that the scan region is to be shifted based on calculated inter-reception-data movement amount, by a scan-region control unit;
creating a plurality of ultrasound images along a time sequence based on one of subharmonic waves along the time sequence and higher harmonic waves along the time sequence separated by the receiving filter from reception data corresponding to an ultrasonic wave transmitted from the ultrasonic probe into shifted scan region, by an image creating unit; and
controlling display of created ultrasound images along the time sequence on a predetermined display unit, by a display control unit and controlling display of the region of interest to remain at a same position on the predetermined display unit based upon the calculation of the movement amount.

12. The method according to claim 11, comprising:
calculating a movement amount of the set region of interest between the created ultrasound images along the time sequence as an inter-image movement amount, by an inter-image movement-amount calculating unit; and
controlling display of the region of interest included in each of the created ultrasound images along the time sequence at a same display position on the predetermined display unit, based on the calculated inter-image movement amount, by the display control unit.

13. The method according to claim 12, comprising:
calculating in real time an inter-image movement amount using a created new ultrasound image each time when a new ultrasound image is created, by the inter-image movement-amount calculating unit; and
controlling display in real time of the region of interest to be included in the new ultrasound image at a same position on the predetermined display unit based on a calculated new inter-image movement amount each time when a new inter-image movement amount is calculated, by the display control unit.

14. The method according to claim 12, comprising:
creating a first ultrasound image that is an ultrasound image based on separated fundamental wave, and a second ultrasound image that is an ultrasound image based on one of separated subharmonic wave and separated higher harmonic wave, along a time sequence, from reception data corresponding to an ultrasonic wave transmitted from the ultrasonic probe into the shifted scan region, by the image creating unit;
calculating the inter-image movement amount between first ultrasound images created along the time sequence, by the inter-image movement-amount calculating unit; and
controlling display of the region of interest at a same position on the predetermined display unit based on calculated inter-image movement amount in each of cases when displaying the second ultrasound image, when displaying the first ultrasound image and the second ultrasound image in parallel, and when displaying the first ultrasound image and the second ultrasound image in a superposed manner, on the predetermined display unit, by the display control unit.

15. The method according to claim 14, comprising:
calculating in real time an inter-reception-data movement amount using a separated new fundamental wave each time when a new fundamental wave is separated, by the inter-reception-data movement-amount calculating unit;
controlling a scan region of an ultrasonic wave to be transmitted from the ultrasonic probe such that the scan region is to be shifted in real time based on a calculated new inter-reception-data movement amount each time when a new inter-reception-data movement amount is calculated, by the scan-region control unit;
creating in real time a first ultrasound image and a second ultrasound image based on reception data corresponding to an ultrasonic wave transmitted from the ultrasonic probe into a shifted scan region, by the image creating unit;
calculating an inter-image movement amount using a created new first ultrasound image each time when a new first ultrasound image and a new second ultrasound image are created, by the inter-image movement-amount calculating unit; and
controlling display in real time of the region of interest at a same display position on the predetermined display unit based on a calculated new inter-image movement amount each time when a new inter-image movement amount is calculated, by the display control unit.

16. The method according to claim 12, wherein the fundamental waves are used for creating B-mode image data.

17. The method according to claim 12, comprising:
controlling the scan region of an ultrasonic wave to be transmitted from the ultrasonic probe such that the scan region is to be shifted after moving a focus position of the ultrasonic wave to be transmitted from the ultrasonic probe, based on the calculated inter-reception-data movement amount, and the focus point is close to the region of interest, by the scan-region control unit.

18. The method according to claim 11, wherein the calculating the inter-reception-data movement amount uses at least one of reception data corresponding to an ultrasonic wave transmitted for calculating the inter-reception-data movement amount, and reception data corresponding to an ultrasonic wave transmitted for creating an ultrasound image to be displayed on the predetermined display unit, by the inter-reception-data movement-amount calculating unit.

19. The method according to claim 11, comprising: controlling the scan region of an ultrasonic wave to be transmitted from the ultrasonic probe such that the scan region is to be shifted after moving a focus position of the ultrasonic wave to be transmitted from the ultrasonic probe, based on the calculated inter-reception-data movement amount, by the scan-region control unit.

20. The method according to claim 11, comprising:
calculating in real time an inter-reception-data movement amount using acquired new reception data each time when new reception data for calculating the inter-reception-data movement amount is acquired, by the inter-reception-data movement-amount calculating unit;
controlling the scan region of an ultrasonic wave to be transmitted from the ultrasonic probe such that the scan region is to be shifted in real time based on a calculated new inter-reception-data movement amount each time when a new inter-reception-data movement amount is calculated, by the scan-region control unit;
creating in real time an ultrasound image based on reception data corresponding to an ultrasonic wave transmitted from the ultrasonic probe into the shifted scan region, by the image creating unit; and
controlling display of a created new ultrasound image in real time on the predetermined display unit each time when a new ultrasound image is created by the display control unit.

* * * * *